United States Patent
Glasberg et al.

(10) Patent No.: US 11,052,254 B2
(45) Date of Patent: *Jul. 6, 2021

(54) METHODS AND SYSTEMS OF ELECTRODE POLARITY SWITCHING IN ELECTRICAL STIMULATION THERAPY

(71) Applicant: EndoStim, Inc., Dallas, TX (US)

(72) Inventors: Ofer Glasberg, Zichron Ya'akov (IL); Shai Policker, Tenafly, NJ (US); Virender K. Sharma, Paradise Valley, AZ (US); Paul V. Goode, Round Rock, TX (US); Bevil Hogg, Murrieta, CA (US)

(73) Assignee: ENDOSTIM (ABC), LLC, San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/794,209

(22) Filed: Oct. 26, 2017

(65) Prior Publication Data

US 2018/0296838 A1    Oct. 18, 2018

Related U.S. Application Data

(63) Continuation of application No. 14/475,736, filed on Sep. 3, 2014, now Pat. No. 9,827,425.

(Continued)

(51) Int. Cl.
    *A61N 1/36*    (2006.01)
    *A61B 5/00*    (2006.01)

(52) U.S. Cl.
    CPC .......... *A61N 1/3615* (2013.01); *A61B 5/4233* (2013.01); *A61B 5/4238* (2013.01);

(Continued)

(58) Field of Classification Search
    None
    See application file for complete search history.

(56) References Cited

U.S. PATENT DOCUMENTS 3,909,883 A    10/1975    Fegen
3,910,281 A    10/1975    Kletschka
(Continued)

FOREIGN PATENT DOCUMENTS

CN    1476339       2/2004
CN    1494451 A     5/2004
(Continued)

OTHER PUBLICATIONS

Supplementary European Search Report for EP14842625, dated Feb. 27, 2017.

(Continued)

*Primary Examiner* — Erica S Lee
(74) *Attorney, Agent, or Firm* — Novel IP

(57) ABSTRACT

Methods for electrically stimulating body tissues to improve function or reduce symptoms provide an electrical stimulation system having two or more electrodes that are capable of being switched independently from a hyperpolarizing (depolarizing) state to a hypopolarizing state. Multiple combinations of hyperpolarizing electrodes and hypopolarizing electrodes are created by polarity switching to determine a polarity configuration having the best performance as determined by symptom reporting and clinical diagnostic tests. Polarity switching is triggered manually or is programmed to be switched automatically. Determining the configuration providing electrical stimulation resulting in the greatest benefit allows the system to be operated with one or more electrodes in a hypopolarizing state, thereby reducing energy requirements, tissue tolerance, and tissue fatigue.

18 Claims, 7 Drawing Sheets

Related U.S. Application Data

(60) Provisional application No. 61/873,229, filed on Sep. 3, 2013.

(52) U.S. Cl.
CPC .......... *A61B 5/4836* (2013.01); *A61B 5/6871* (2013.01); *A61N 1/36007* (2013.01); *A61N 1/36132* (2013.01); *A61N 1/36185* (2013.01); *A61N 1/36139* (2013.01)

(56) References Cited

U.S. PATENT DOCUMENTS

| | | |
|---|---|---|
| 4,393,883 A | 7/1983 | Smyth |
| 4,414,986 A | 11/1983 | Dickhudt |
| 4,612,934 A | 9/1986 | Borkan |
| 4,735,205 A | 4/1988 | Chachques |
| 5,117,827 A | 6/1992 | Stuebe |
| 5,188,104 A | 2/1993 | Wernicke |
| 5,193,539 A | 3/1993 | Schulman |
| 5,197,491 A | 3/1993 | Anderson |
| 5,231,988 A | 8/1993 | Wernicke |
| 5,263,480 A | 11/1993 | Wernicke |
| 5,292,344 A | 3/1994 | Douglas |
| 5,360,428 A | 11/1994 | Hutchinson, Jr. |
| 5,423,872 A | 6/1995 | Cigaina |
| 5,531,778 A | 7/1996 | Maschino |
| 5,540,730 A | 7/1996 | Terry, Jr. |
| 5,556,425 A | 9/1996 | Hewson |
| 5,606,242 A | 2/1997 | Hull |
| 5,633,573 A | 5/1997 | van Phuoc |
| 5,649,902 A | 7/1997 | Yoon |
| 5,674,205 A | 10/1997 | Pasricha |
| 5,690,691 A | 11/1997 | Chen |
| 5,697,375 A | 12/1997 | Hickey |
| 5,709,224 A | 1/1998 | Behl |
| 5,716,385 A | 2/1998 | Mittal |
| 5,716,392 A | 2/1998 | Bourgeois |
| 5,769,881 A | 6/1998 | Schroeppel |
| 5,810,810 A | 9/1998 | Tay |
| 5,836,994 A | 11/1998 | Bourgeois |
| 5,861,014 A | 1/1999 | Familoni |
| 5,861,044 A | 1/1999 | Crenshaw |
| 5,882,340 A | 3/1999 | Yoon |
| 5,893,883 A | 4/1999 | Torgerson |
| 5,935,126 A | 8/1999 | Riza |
| 5,995,872 A | 11/1999 | Bourgeois |
| 6,006,755 A | 12/1999 | Edwards |
| 6,026,326 A | 2/2000 | Bardy |
| 6,041,258 A | 3/2000 | Cigaina |
| 6,051,017 A | 4/2000 | Loeb |
| 6,091,992 A | 7/2000 | Bourgeois |
| 6,097,984 A | 8/2000 | Douglas |
| 6,216,039 B1 | 4/2001 | Bourgeois |
| 6,221,039 B1 | 4/2001 | Durgin |
| 6,243,607 B1 | 6/2001 | Mintchev |
| 6,254,598 B1 | 7/2001 | Edwards |
| 6,285,897 B1 | 9/2001 | Kilcoyne |
| 6,321,124 B1 | 11/2001 | Cigaina |
| 6,360,130 B1 | 3/2002 | Duysens |
| 6,381,495 B1 | 4/2002 | Jenkins |
| 6,449,511 B1 | 9/2002 | Mintchev |
| 6,510,332 B1 | 1/2003 | Greenstein |
| 6,542,776 B1 | 4/2003 | Gordon |
| 6,571,127 B1 | 5/2003 | Ben-Haim |
| 6,587,719 B1 | 7/2003 | Barrett |
| 6,591,137 B1 | 7/2003 | Fischell |
| 6,606,523 B1 | 8/2003 | Jenkins |
| 6,611,715 B1 | 8/2003 | Boveja |
| 6,612,983 B1 | 9/2003 | Marchal |
| 6,615,084 B1 | 9/2003 | Cigaina |
| 6,678,561 B2 | 1/2004 | Forsell |
| 6,684,104 B2 | 1/2004 | Gordon |
| 6,749,607 B2 | 6/2004 | Edwards |
| 6,754,536 B2 | 6/2004 | Swoyer |
| 6,760,626 B1 | 7/2004 | Boveja |
| 6,820,019 B1 | 11/2004 | Kelly |
| 6,826,428 B1 | 11/2004 | Chen |
| 6,832,114 B1 | 12/2004 | Whitehurst |
| 6,853,862 B1 | 2/2005 | Marchal |
| 6,876,885 B2 | 4/2005 | Swoyer |
| 6,879,859 B1 | 4/2005 | Boveja |
| 6,879,861 B2 | 4/2005 | Benz |
| 6,901,295 B2 | 5/2005 | Sharma |
| 6,915,165 B2 | 7/2005 | Forsell |
| 6,947,792 B2 | 9/2005 | Ben-Haim |
| 6,952,613 B2 | 10/2005 | Swoyer |
| 7,006,871 B1 | 2/2006 | Darvish |
| 7,016,735 B2 | 3/2006 | Imran |
| 7,054,689 B1 | 5/2006 | Whitehurst |
| 7,054,690 B2 | 5/2006 | Imran |
| 7,076,305 B2 | 7/2006 | Imran |
| 7,076,306 B2 | 7/2006 | Marchal |
| 7,087,053 B2 | 8/2006 | Vanney |
| 7,114,502 B2 | 10/2006 | Schulman |
| 7,120,498 B2 | 10/2006 | Imran |
| 7,146,216 B2 | 12/2006 | Bumm |
| 7,167,750 B2 | 1/2007 | Knudson |
| 7,177,693 B2 | 2/2007 | Starkebaum |
| 7,200,443 B2 | 4/2007 | Faul |
| 7,203,551 B2 | 4/2007 | Houben |
| 7,255,675 B2 | 8/2007 | Gertner |
| 7,263,405 B2 | 8/2007 | Boveja |
| 7,299,091 B2 | 11/2007 | Barrett |
| 7,310,557 B2 | 12/2007 | Maschino |
| 7,340,306 B2 | 3/2008 | Barrett |
| 7,343,201 B2 | 3/2008 | Mintchev |
| 7,363,084 B2 | 4/2008 | Kurokawa |
| 7,444,183 B2 | 10/2008 | Knudson |
| 7,477,994 B2 | 1/2009 | Sunshine |
| 7,519,431 B2 | 4/2009 | Goetz |
| 7,519,433 B2 | 4/2009 | Foley |
| 7,558,629 B2 | 7/2009 | Keimel |
| 7,593,777 B2 | 9/2009 | Gerber |
| 7,599,736 B2 | 10/2009 | DiLorenzo |
| 7,620,454 B2 | 11/2009 | Dinsmoor |
| 7,664,551 B2 | 2/2010 | Cigaina |
| 7,676,270 B2 | 3/2010 | Imran |
| 7,702,394 B2 | 4/2010 | Imran |
| 7,702,395 B2 | 4/2010 | Towe |
| 7,702,934 B2 | 4/2010 | Imran |
| 7,711,437 B1 | 5/2010 | Bornzin |
| 7,720,539 B2 | 5/2010 | Mintchev |
| 7,729,771 B2 | 6/2010 | Knudson |
| 7,734,355 B2 | 6/2010 | Cohen |
| 7,738,961 B2 | 6/2010 | Sharma |
| 7,742,818 B2 | 6/2010 | Dinsmoor |
| 7,794,425 B2 | 9/2010 | Gobel |
| 7,809,442 B2 | 10/2010 | Bolea |
| 7,813,809 B2 | 10/2010 | Strother |
| 7,835,796 B2 | 11/2010 | Maschino |
| 7,848,802 B2 | 12/2010 | Goetz |
| 7,899,540 B2 | 3/2011 | Maschino |
| 7,914,468 B2 | 3/2011 | Shalon |
| 7,941,221 B2 | 5/2011 | Foley |
| 7,957,807 B2 | 6/2011 | Starkebaum |
| 7,962,214 B2 | 6/2011 | Byerman |
| 7,983,755 B2 | 7/2011 | Starkebaum |
| 8,135,470 B2 | 3/2012 | Keimel |
| 8,155,758 B2 | 4/2012 | Roline |
| 8,160,709 B2 | 4/2012 | Soffer |
| 8,185,206 B2 | 5/2012 | Starkebaum |
| 8,282,561 B2 | 10/2012 | Towe |
| 8,380,321 B2 | 2/2013 | Goetz |
| 8,406,868 B2 | 3/2013 | Buschman |
| 8,423,134 B2 | 4/2013 | Buschman |
| 8,447,403 B2 | 5/2013 | Sharma |
| 8,447,404 B2 | 5/2013 | Sharma |
| 8,452,407 B2 | 5/2013 | Whitehurst |
| 8,467,874 B2 | 6/2013 | Chen |
| 8,467,884 B2 | 6/2013 | Chen |
| 8,521,292 B2 | 8/2013 | Wei |
| 8,538,532 B2 | 9/2013 | Starkebaum |
| 8,538,534 B2 | 9/2013 | Soffer |

(56) References Cited

U.S. PATENT DOCUMENTS

| | | |
|---|---|---|
| 8,543,210 B2 | 9/2013 | Sharma |
| 8,556,952 B2 | 10/2013 | Shadduck |
| 8,594,811 B2 | 11/2013 | Chen |
| 8,712,529 B2 | 4/2014 | Sharma |
| 8,712,530 B2 | 4/2014 | Sharma |
| 8,718,771 B2 | 5/2014 | Gandhi |
| 8,761,903 B2 | 6/2014 | Chen |
| 8,792,986 B2 | 7/2014 | Cigaina |
| 8,831,737 B2 | 9/2014 | Wesselink |
| 8,892,217 B2 | 11/2014 | Camps |
| 9,020,597 B2 | 4/2015 | Sharma |
| 9,037,245 B2 | 5/2015 | Sharma |
| 9,061,147 B2 | 6/2015 | Sharma |
| 9,498,619 B2 | 11/2016 | Goode |
| 2001/0041831 A1 | 11/2001 | Starkweather |
| 2002/0103522 A1 | 8/2002 | Swoyer |
| 2002/0138075 A1 | 9/2002 | Edwards |
| 2002/0161414 A1 | 10/2002 | Flesler |
| 2002/0165589 A1 | 11/2002 | Imran |
| 2003/0014086 A1 | 1/2003 | Sharma |
| 2003/0028226 A1 | 2/2003 | Thompson |
| 2003/0055463 A1 | 3/2003 | Gordon |
| 2003/0078633 A1 | 4/2003 | Firlik |
| 2003/0120321 A1 | 6/2003 | Bumm |
| 2003/0144708 A1 | 7/2003 | Starkebaum |
| 2003/0195600 A1 | 10/2003 | Tronnes |
| 2004/0010290 A1 | 1/2004 | Schroeppel |
| 2004/0012088 A1 | 1/2004 | Fukasawa |
| 2004/0015201 A1 | 1/2004 | Greenstein |
| 2004/0024428 A1 | 2/2004 | Barrett |
| 2004/0039427 A1 | 2/2004 | Barrett |
| 2004/0044376 A1 | 3/2004 | Flesler |
| 2004/0059393 A1 | 3/2004 | Policker |
| 2004/0073453 A1 | 4/2004 | Nenov |
| 2004/0088033 A1 | 5/2004 | Smits |
| 2004/0116977 A1 | 6/2004 | Finch |
| 2004/0138586 A1 | 7/2004 | RobertGanz |
| 2004/0147976 A1 | 7/2004 | Gordon |
| 2004/0167583 A1 | 8/2004 | Knudson |
| 2004/0172088 A1 | 9/2004 | Knudson |
| 2004/0186544 A1 | 9/2004 | King |
| 2004/0193229 A1 | 9/2004 | Starkebaum |
| 2004/0236381 A1 | 11/2004 | Dinsmoor |
| 2004/0236382 A1 | 11/2004 | Dinsmoor |
| 2004/0243182 A1 | 12/2004 | Cohen |
| 2005/0027328 A1 | 2/2005 | Greenstein |
| 2005/0049655 A1 | 3/2005 | Boveja |
| 2005/0065571 A1 | 3/2005 | Imran |
| 2005/0070974 A1 | 3/2005 | Knudson |
| 2005/0075678 A1 | 4/2005 | Faul |
| 2005/0090873 A1 | 4/2005 | Imran |
| 2005/0131485 A1 | 6/2005 | Knudson |
| 2005/0131486 A1 | 6/2005 | Boveja |
| 2005/0137480 A1 | 6/2005 | Alt |
| 2005/0137643 A1 | 6/2005 | Mintchev |
| 2005/0137644 A1 | 6/2005 | Boveja |
| 2005/0143787 A1 | 6/2005 | Boveja |
| 2005/0149141 A1 | 7/2005 | Starkebaum |
| 2005/0149142 A1 | 7/2005 | Starkebaum |
| 2005/0149146 A1 | 7/2005 | Boveja |
| 2005/0222637 A1 | 10/2005 | Chen |
| 2005/0222638 A1 | 10/2005 | Foley |
| 2005/0245788 A1 | 11/2005 | Gerber |
| 2005/0251219 A1 | 11/2005 | Evans |
| 2006/0004304 A1 | 1/2006 | TomParks |
| 2006/0015162 A1 | 1/2006 | Edward |
| 2006/0036293 A1 | 2/2006 | Whitehurst |
| 2006/0041277 A1 | 2/2006 | Deem |
| 2006/0047323 A1 | 3/2006 | Foley |
| 2006/0064037 A1 | 3/2006 | Shalon |
| 2006/0074459 A1 | 4/2006 | Flesler |
| 2006/0089699 A1 | 4/2006 | Imran |
| 2006/0095077 A1 | 5/2006 | Tronnes |
| 2006/0106442 A1 | 5/2006 | Richardson |
| 2006/0116736 A1 | 6/2006 | DiLorenzo |
| 2006/0122660 A1 | 6/2006 | Boveja |
| 2006/0149337 A1 | 7/2006 | John |
| 2006/0167498 A1 | 7/2006 | DiLorenzo |
| 2006/0200217 A1 | 9/2006 | Wessman |
| 2006/0206160 A1 | 9/2006 | Cigaina |
| 2006/0218011 A1 | 9/2006 | Walker |
| 2006/0247717 A1 | 11/2006 | Starkebaum |
| 2006/0247718 A1 | 11/2006 | Starkebaum |
| 2006/0247719 A1 | 11/2006 | Maschino |
| 2006/0247721 A1 | 11/2006 | Maschino |
| 2006/0247722 A1 | 11/2006 | Maschino |
| 2006/0265021 A1 | 11/2006 | Herbert |
| 2006/0270989 A1 | 11/2006 | McMichael |
| 2007/0016274 A1 | 1/2007 | Boveja |
| 2007/0049793 A1 | 3/2007 | Ignagni |
| 2007/0060955 A1 | 3/2007 | Strother |
| 2007/0060968 A1 | 3/2007 | Strother |
| 2007/0060979 A1 | 3/2007 | Strother |
| 2007/0066995 A1 | 3/2007 | Strother |
| 2007/0067000 A1 | 3/2007 | Strother |
| 2007/0100388 A1 | 5/2007 | Gerber |
| 2007/0106337 A1 | 5/2007 | Errico |
| 2007/0106338 A1 | 5/2007 | Errico |
| 2007/0114971 A1 | 5/2007 | Uesaka |
| 2007/0142699 A1 | 6/2007 | SallyJandrall |
| 2007/0142831 A1 | 6/2007 | Shadduck |
| 2007/0142884 A1 | 6/2007 | SallyJandrall |
| 2007/0156182 A1 | 7/2007 | Castel |
| 2007/0162084 A1 | 7/2007 | Chen |
| 2007/0162085 A1 | 7/2007 | DiLorenzo |
| 2007/0179542 A1 | 8/2007 | Prakash |
| 2007/0238942 A1 | 10/2007 | Baylor |
| 2007/0239248 A1 | 10/2007 | Hastings |
| 2007/0244375 A1 | 10/2007 | Jenkins |
| 2007/0255118 A1 | 11/2007 | Miesel |
| 2007/0255335 A1 | 11/2007 | Herbert |
| 2007/0255336 A1 | 11/2007 | Herbert |
| 2007/0255352 A1 | 11/2007 | Roline |
| 2007/0265662 A1 | 11/2007 | Ufford |
| 2007/0265666 A1 | 11/2007 | Roberts |
| 2007/0265668 A1 | 11/2007 | Reinke |
| 2007/0265671 A1 | 11/2007 | Roberts |
| 2007/0265674 A1 | 11/2007 | Olson |
| 2007/0282410 A1 | 12/2007 | Cross |
| 2007/0293910 A1 | 12/2007 | Strother |
| 2007/0299481 A1 | 12/2007 | Syed |
| 2008/0021512 A1 | 1/2008 | Knudson |
| 2008/0039904 A1 | 2/2008 | Bulkes |
| 2008/0046062 A1 | 2/2008 | Camps |
| 2008/0058836 A1 | 3/2008 | Moll |
| 2008/0058891 A1 | 3/2008 | Ben-Haim |
| 2008/0086179 A1 | 4/2008 | Sharma |
| 2008/0132968 A1 | 6/2008 | Starkebaum |
| 2008/0147137 A1 | 6/2008 | Cohen |
| 2008/0154191 A1 | 6/2008 | Gobel |
| 2008/0183238 A1 | 7/2008 | Chen |
| 2008/0195171 A1 | 8/2008 | Sharma |
| 2008/0208355 A1 | 8/2008 | Stack |
| 2009/0012421 A1 | 1/2009 | Bek |
| 2009/0018617 A1 | 1/2009 | Skelton |
| 2009/0018619 A1 | 1/2009 | Skelton |
| 2009/0020406 A1 | 1/2009 | Nirmalakhandan |
| 2009/0030475 A1 | 1/2009 | Brynelsen |
| 2009/0069803 A1 | 3/2009 | Starkebaum |
| 2009/0076498 A1 | 3/2009 | Saadat |
| 2009/0088817 A1 | 4/2009 | Starkebaum |
| 2009/0131993 A1* | 5/2009 | Rousso ............. A61N 1/36007 607/2 |
| 2009/0132001 A1 | 5/2009 | Soffer |
| 2009/0187223 A1 | 7/2009 | Gross |
| 2009/0192564 A1 | 7/2009 | Armstrong |
| 2009/0204063 A1 | 8/2009 | Policker |
| 2009/0210019 A1 | 8/2009 | Kim |
| 2009/0264951 A1* | 10/2009 | Sharma ................ A61N 1/05 607/40 |
| 2009/0281553 A1 | 11/2009 | Kalloo |
| 2010/0004648 A1 | 1/2010 | Edwards |
| 2010/0010388 A1 | 1/2010 | Panken |
| 2010/0049026 A1 | 2/2010 | Gerber |

(56) References Cited

U.S. PATENT DOCUMENTS

| | | |
|---|---|---|
| 2010/0057085 A1 | 3/2010 | Holcomb |
| 2010/0069789 A1 | 3/2010 | Hirota |
| 2010/0076345 A1 | 3/2010 | Soffer |
| 2010/0170812 A1 | 7/2010 | Odierno |
| 2010/0198039 A1 | 8/2010 | Towe |
| 2010/0268495 A1 | 10/2010 | Armstrong |
| 2010/0324432 A1 | 12/2010 | Bjoerling |
| 2011/0004266 A1 | 1/2011 | Sharma |
| 2011/0034967 A1 | 2/2011 | Chen |
| 2011/0046653 A1 | 2/2011 | Addington |
| 2011/0071589 A1 | 3/2011 | Starkebaum |
| 2011/0213437 A9 | 9/2011 | Armstrong |
| 2011/0224665 A1* | 9/2011 | Crosby .............. A61B 18/1492 606/33 |
| 2011/0295335 A1 | 12/2011 | Sharma |
| 2011/0295336 A1 | 12/2011 | Sharma |
| 2011/0307023 A1 | 12/2011 | Tweden |
| 2011/0307027 A1 | 12/2011 | Sharma |
| 2011/0307028 A1 | 12/2011 | Sharma |
| 2012/0232610 A1 | 9/2012 | Soffer |
| 2012/0259389 A1 | 10/2012 | Starkebaum |
| 2012/0265103 A1 | 10/2012 | Policker |
| 2012/0277619 A1 | 11/2012 | Starkebaum |
| 2012/0296166 A1 | 11/2012 | Kim |
| 2012/0310317 A1 | 12/2012 | Lund |
| 2013/0030503 A1 | 1/2013 | Yaniv |
| 2013/0035740 A1 | 2/2013 | Sharma |
| 2013/0072928 A1 | 3/2013 | Schaer |
| 2013/0090551 A1 | 4/2013 | Sharma |
| 2013/0178912 A1 | 7/2013 | Sharma |
| 2013/0218229 A1 | 8/2013 | Sharma |
| 2013/0231660 A1 | 9/2013 | Edwards |
| 2013/0238048 A1 | 9/2013 | Almendinger |
| 2014/0012348 A1 | 1/2014 | Starkebaum |
| 2014/0018657 A1 | 1/2014 | Sharma |
| 2014/0081366 A1 | 3/2014 | Bentley |
| 2014/0088664 A1 | 3/2014 | Sharma |
| 2014/0088666 A1 | 3/2014 | Goetz |
| 2014/0135886 A1 | 5/2014 | Cook |
| 2014/0222106 A1 | 8/2014 | Sharma |
| 2014/0228911 A1 | 8/2014 | Sharma |
| 2014/0243593 A1 | 8/2014 | Goode |
| 2015/0045786 A1 | 2/2015 | Edwards |
| 2015/0119952 A1 | 4/2015 | Sharma |
| 2016/0001071 A1 | 1/2016 | Sharma |
| 2016/0045730 A1 | 2/2016 | Kim |
| 2017/0224986 A1 | 8/2017 | Imran |

FOREIGN PATENT DOCUMENTS

| | | |
|---|---|---|
| CN | 102725021 | 10/2012 |
| CN | 105641805 A | 6/2016 |
| EP | 1004330 | 5/2000 |
| EP | 1004330 A1 | 5/2000 |
| WO | 199853878 | 12/1998 |
| WO | 9903532 | 1/1999 |
| WO | 9930776 | 6/1999 |
| WO | 0061223 A1 | 10/2000 |
| WO | 0061224 A1 | 10/2000 |
| WO | 2000061223 | 10/2000 |
| WO | 2000061224 | 10/2000 |
| WO | 0238217 A2 | 5/2002 |
| WO | 0243467 A2 | 6/2002 |
| WO | 2002043467 | 6/2002 |
| WO | 02089655 | 11/2002 |
| WO | 2002100481 A1 | 12/2002 |
| WO | 2005051486 A1 | 9/2005 |
| WO | 2007137026 | 11/2007 |
| WO | 2008117296 A1 | 10/2008 |
| WO | 2009009276 | 1/2009 |
| WO | 2009114008 A1 | 9/2009 |
| WO | 2010027963 | 3/2010 |
| WO | 2010135634 | 11/2010 |
| WO | 2012151449 | 11/2012 |
| WO | 2014032030 | 2/2014 |
| WO | 2015034867 | 3/2015 |
| WO | 2015077425 | 5/2015 |
| WO | 2015077435 | 5/2015 |

OTHER PUBLICATIONS

Christensen et al., 'Physiologic Specialization at Esophagogastric Junction in Three Species', American Journal of Physiology, vol. 225, No. 6, Dec. 1973, 1265-1270.

Cigaina, Valerio; Long-term Follow-Up of Gastric Stimulation for Obesity: The Mestre 8-Year Experience; Obesity Surgery; 14; 2004; S14-22.

Clarke et al,. 'An Endoscopic Implantable Device Stimulates the LES On-Demand by Remote Control in a Canine Model'; Gastrointestinal Endoscopy, vol. 63, No. 5; 2006, AB103, 759.

Clarke et al., 'An endoscopically implantable device stimulates the lower esophageal sphincter on demand by remote control: a study using a canine model', Endoscopy 2007; 39: 72-76.

Ellis, et al., 'The Prevention of Experimentally Induced Reflux by Electrical Stimulation of the Distal Esophagus', American Journal of Surgery, vol. 115, Apr. 1968, 482-487.

EPO Search Report EP09704463, dated Jan. 10, 2011, Virender K. Sharma.

European Search Opinion for EP20120779639, Virender K. Sharma, dated Nov. 25, 2014.

First Office Action for Application No. CN 01819456, dated Nov. 18, 2014.

Gonzalez et al., 'Different Responsiveness of Excitatory and Inhibitory Enteric Motor Neurons in the Human Esophagus to Electrical Field Stimulation and to Nicotine', Am J Physiol Gastrointest Liver Physiol, 287:G299-G306, 2004.

International Search Report for PCT/US12/053576, dated Dec. 24, 2012.

International Search Report for PCT/US2007/068907, dated Aug. 7, 2008.

International Search Report for PCT/US2008/053780, dated Jun. 8, 2009.

International Search Report for PCT/US2008/056479, dated Aug. 20, 2008.

International Search Report for PCT/US2011/027243, dated Jul. 8, 2011.

International Search Report for PCT/US2012/033695, dated Aug. 7, 2012.

International Search Report for PCT/US2012/036408, dated Aug. 17, 2012.

International Search Report for PCT/US2013/056520, dated Apr. 4, 2014.

International Search Report for PCT/US2014/053793, dated Mar. 27, 2015.

International Search Report for PCT/US2014/066565, dated Mar. 12, 2015.

International Search Report for PCT/US2014/066578, dated Mar. 19, 2015.

Jameison, GG et al. "Laparoscopic Nissen Fundoplication". Annals of Surgery, vol. 220. No. 2, p. 139 (1994).

Kahrilas et al., 'Impact of Fundoplication on Bolus Transit Across Esophagogastric Junction', American Physiological Society, 1998, 1386-1393.

Kamath et al., 'Neurocardiac and Cerebral Responses Evoked by Esophageal Vago-Afferent Stimulation in Humans: Effects of Varying Intensities', Cardiovascular Research, 40 (1998) 591-599.

Kantsevoy et al., 'An Endoscopically Implantable On-Demand Stimulator is Successful in Increasing Lower Esophageal Sphincter Pressure in a Porcine Model'; Gastrointestinal Endoscopy, vol. 61, No. 5: 2005, AB79, 222.

Lund et al., 'Electrical Stimulation of Esophageal Smooth Muscle and Effects of Antagonists', American Journal of Physiology, vol. 217, No. 5, Nov. 1969, 1369-1374.

Notice of Allowance dated Apr. 3, 2014 for U.S. Appl. No. 13/447,168.
Notice of Allowance dated Dec. 24, 2014 for U.S. Appl. No. 13/463,803.

(56) References Cited

OTHER PUBLICATIONS

Notice of Allowance dated Feb. 20, 2015 for U.S. Appl. No. 14/201,645.
Notice of Allowance dated Jan. 20, 2015 for U.S. Appl. No. 13/602,184.
Notice of Allowance dated Jul. 21, 2014 for U.S. Appl. No. 13/447,168.
Notice of Allowance dated Mar. 17, 2014 for U.S. Appl. No. 13/447,168.
Office Action dated Apr. 11, 2014 for U.S. Appl. No. 13/602,184.
Office Action dated Feb. 1, 2016 for U.S. Appl. No. 14/475,736.
Office Action dated Feb. 20, 2015 for U.S. Appl. No. 14/175,927.
Office Action dated Jul. 8, 2014 for U.S. Appl. No. 13/463,803.
Office Action dated Jun. 19, 2015 for U.S. Appl. No. 13/975,162.
Office Action dated Jun. 25, 2015 for U.S. Appl. No. 14/201,766.
Office Action dated Jun. 8, 2016 for U.S. Appl. No. 14/475,736.
Office Action dated Oct. 2, 2015 for U.S. Appl. No. 14/500,856.
Office Action dated Oct. 7, 2015 for U.S. Appl. No. 13/975,162.
Sallam et al, 'Feasibility of gastric electrical stimulation by percutaneous endoscopic transgastric electrodes'; Gastrointestinal Endoscopy; vol. 68, No. 4; 2008, 754-759.
Sanmiguel et al, 'Effect of electrical stimulation of the LES on LES pressure in a canine model'; Am J Physiol Gastrointest Live Physiol; 295: 389-394; 2008.
Shellock, Frank G. 'RF Bion Microstimulator' MRISafety.com, http://www.mrisafety.com/SafetyInfov.asp?SafetyInfoID=254, Shellock R & D Services, Inc. and Frank G. Shellock, Ph.D., 4 pages, 2014.
Stein et al., 'Three-dimensional Imaging of the Lower Esophageal Sphincter in Gastroesophageal Reflux Disease,' Annual Meeting of the American Surgical Association, Apr. 11-13, 1991, 374-383.
Summary of Neurostimulation Systems Features, Advanced Neuromodulation Systems (ANS) home page, accessed on May 31, 2007 at http://web.archive.org/web/20040211224857/www.ans-medical.com/patients/WhichSystemIsBest/SumOfNeurostimulation.html.
Supplementary European Search Report for EP20120779639, Virender K. Sharma, dated Nov. 13, 2014.
Tam, WCE et al. "Delivery of radiofrequency energy to the lower esophageal sphincter and gastric cardia inhibits transient oesophageal sphincter relaxations and gastro-oesophageal reflux in patients with reflux disease". Gut, 52(4), 479-785 (2003).
Xing et al, 'Gastric Electrical Stimulation (GES) with Parameters for Morbid Obesity Elevates Lower Esophageal Sphincter (LES) Pressure in Conscious Dogs'; Obesity Surgery; 15; 2005; pp. 1321-1327.
Xing et al, 'Gastric Electrical Stimulation Significantly Increases Canine Lower Esophageal Sphincter Pressure'; Digestive Diseases and Sciences; vol. 50, No. 8 (Aug. 2005), pp. 1481-1487.
Xing et al., 'Gastric Electrical Stimulation Significantly Increases Canine Lower Esophageal Pressure' Gastroenterology 122: May Issue, A579, 2003. Presented as a poster at Digestive Disease Week in Orlando, FL on Monday, May 19, 2003.
Office Action dated May 20, 2016 for U.S. Appl. No. 13/975,162.
Office Action dated May 4, 2016 for U.S. Appl. No. 14/548,793.
Notice of Allowance dated Jul. 19, 2016 for U.S. Appl. No. 14/191,085.
Supplementary European Search Report for EP13831668, completed on Apr. 15, 2016.
Office Action dated Aug. 24, 2016 for U.S. Appl. No. 14/753,402.
Office Action dated Aug. 19, 2016 for U.S. Appl. No. 14/943,772.
Notice of Allowance dated Jan. 20, 2016 for U.S. Appl. No. 14/201,766.
Examination Report for Australian Patent Application No. 2012242533, dated Oct. 5, 2015.
Office Action for Chinese Patent Application No. 201280028867.7, dated May 4, 2015.
Extended European Search Report for EPO Application No. 12771852.6, dated Aug. 28, 2014.
Examination Report for Australian Patent Application No. 2012250686, dated Nov. 4, 2015.
Examination Report for New Zealand Patent Application No. 616944, dated Jun. 17, 2014.
Examination Report for New Zealand Patent Application No. 616944, dated Nov. 2, 2015.
Second Office Action for Chinese Patent Application No. 201280028867.7, dated Mar. 21, 2016.
First Office Action for Chinese Patent Application No. 201380054290.1, dated Apr. 1, 2016.
Office Action dated Mar. 10, 2016 for U.S. Appl. No. 14/191,085.
Office Action dated Mar. 15, 2016 for U.S. Appl. No. 14/695,267.
Office Action dated Mar. 17, 2016 for U.S. Appl. No. 14/500,856.
Office Action dated Jan. 18, 2017 for U.S. Appl. No. 14/475,736.
Notice of Allowance dated Jul. 28, 2017 for U.S. Appl. No. 14/475,736.
Notice of Allowance dated Sep. 27, 2016 for U.S. Appl. No. 14/500,856.
Office Action dated Oct. 3, 2016 for U.S. Appl. No. 14/548,793.
Second Office Action for Chines Patent Application No. 201380054290.1, dated Oct. 26, 2016.
Extended European Search Report for EPO Application No. 16174071.7, dated Oct. 19, 2016.
International Search Report for PCT/US2015/061108, dated May 26, 2016.
Notice of Allowance dated Dec. 5, 2016 for U.S. Appl. No. 13/975,162.
Office Action dated Dec. 19, 2016 for U.S. Appl. No. 14/753,402.
Notice of Allowance dated Feb. 16, 2017 for U.S. Appl. No. 14/943,772.
Notice of Allowance dated Apr. 4, 2017 for U.S. Appl. No. 14/548,793.
Office Action dated Apr. 4, 2017 for U.S. Appl. No. 14/753,402.
Examination Report for EP117514430, dated May 17, 2017.
Supplementary European Search Report for EP14863570, dated Jun. 30, 2017.
Supplementary European Search Report for EP14864930, dated May 4, 2017.
Office Action dated Aug. 21, 2017 for U.S. Appl. No. 14/753,402 (pp. 1-9).
Notice of Allowance dated Nov. 8, 2017 for U.S. Appl. No. 14/548,855 (pp. 1-8).
Office Action dated Dec. 20, 2017 for U.S. Appl. No. 14/753, 402 (pp. 1-9).
Office Action dated Jan. 26, 2016 for U.S. Appl. No. 14/686,996.
Office Action dated Oct. 17, 2017 for U.S. Appl. No. 14/686,996 (pp. 1-13).
Office Action dated Dec. 21, 2017 for U.S. Appl. No. 15/594,903.
Examination Report for EP117514430, dated Jan. 17, 2018.
Office Action dated Aug. 10, 2017 for U.S. Appl. No. 15/170,462 (pp. 1-6).
Office Action dated Mar. 8, 2018 for U.S. Appl. No. 15/170,462 (pp. 1-5).
Office Action dated Jun. 18, 2015 for U.S. Appl. No. 14/337,006.
Office Action dated Oct. 7, 2015 for U.S. Appl. No. 14/337,006.
Notice of Allowance dated Mar. 2, 2016 for U.S. Appl. No. 14/337,006.
Extended European Search Report for EP17187374.8, dated Feb. 27, 2018.
First Examination Report for New Zealand Patent Application No. 715619, dated Jan. 22, 2016.
Office Action dated Feb. 12, 2016 for U.S. Appl. No. 14/665,226.
Office Action dated Jul. 5, 2016 for U.S. Appl. No. 14/665,226.
Notice of Allowance dated Nov. 29, 2016 for U.S. Appl. No. 14/665,226.
Office Action dated May 10, 2018 for U.S. Appl. No. 14/753,402 (pp. 1-9).
Office Action dated Jul. 19, 2018 for U.S. Appl. No. 14/686,996 (pp. 1-17).
Office Action dated Jul. 26, 2018 for U.S. Appl. No. 15/443,983 (pp. 1-5).
Examination Report for EP16174071.7, dated Jul. 26, 2018.
Office Action dated Jun. 29, 2018 for U.S. Appl. No. 15/448,944 (pp. 1-6).

(56) References Cited

OTHER PUBLICATIONS

International Search Report for PCT/US2018/025092, dated Jun. 27, 2018.
Examination Report for EP117514430, dated Sep. 14, 2018.
Office Action dated Dec. 4, 2018 for U.S. Appl. No. 14/753,402 (pp. 1-9).
Examination Report for EP14863570.9, dated Oct. 26, 2018.
Notice of Allowance dated Dec. 11, 2018 for U.S. Appl. No. 15/443,983 (pp 1-7).
Office Action dated Dec. 18, 2018 for U.S. Appl. No. 15/639,590 (pp. 1-10).
Corrected Notice of Allowability dated Jan. 28, 2019 for U.S. Appl. No. 15/443,983 (pp. 1-5).
Office Action dated Jan. 25, 2019 for U.S. Appl. No. 15/448,944 (pp. 1-8).

* cited by examiner

METHODS AND SYSTEMS OF ELECTRODE POLARITY SWITCHING IN ELECTRICAL STIMULATION THERAPY

CROSS-REFERENCE

The present application is a continuation application of U.S. patent application Ser. No. 14/475,736, entitled "Methods and Systems of Electrode Polarity Switching in Electrical Stimulation Therapy" and filed on Sep. 3, 2014, which relies on U.S. Provisional Patent Application No. 61/873,229, of the same title and filed on Sep. 3, 2013. Both applications are herein incorporated by reference in their entirety.

The present application is also related to U.S. patent application Ser. No. 14/201,766, entitled "Device and Implantation System for Electrical Stimulation of Biological Systems" and filed on Mar. 7, 2014, which is herein incorporated by reference in its entirety.

FIELD

The present specification relates generally to therapies involving the electrical stimulation of biological systems. More particularly, the present specification relates to methods and systems of changing the polarity of electrical stimulating electrodes to improve therapy efficacy and reduce tissue fatigue.

BACKGROUND

Electrical stimulation of nerves and surrounding tissue is used to treat a variety of conditions. For example, electrical stimulation can be used to restore partial function to limbs or organs following traumatic injury. Electrical stimulation can also be used to reduce pain. Specifically, electrical stimulation can be used to treat disorders associated with the gastrointestinal (GI) system, such as, obesity and gastroesophageal reflux disease (GERD).

Electrical stimulation therapy systems typically comprise an electrical pulse generator and one or more stimulation leads. The leads include one or more exposed electrodes connected to the pulse generator by one or more elongate, insulated wires. The leads are typically anchored in place such that the electrodes are positioned and remain proximate the target nerve or tissues. The pulse generator can often be programmed with respect to pulse amplitude, frequency, and duration.

Gastric electrical stimulation (GES) is a therapy aimed at treating both obesity and GERD. GES employs an implantable, pacemaker-like device to deliver low-level electrical stimulation to the gastrointestinal tract. For obesity, GES operates by disrupting the motility cycle and/or stimulating the enteric nervous system, thereby increasing the duration of satiety experienced by the patient. The procedure involves the surgeon suturing electrical leads to the outer lining of the stomach wall. The leads are then connected to the device, which is implanted just under the skin in the abdomen. Using an external programmer that communicates with the device, the surgeon establishes the level of electrical stimulation appropriate for the patient. The Abiliti® implantable gastric stimulation device, manufactured by IntraPace, is currently available in Europe for treatment of obesity.

In another example, Medtronic offers for sale and use the Enterra™ Therapy, which is indicated for the treatment of chronic nausea and vomiting associated with gastroparesis when conventional drug therapies are not effective. The Enterra™ Therapy uses mild electrical pulses to stimulate the stomach. According to Medtronic, this electrical stimulation helps control the symptoms associated with gastroparesis, including nausea and vomiting.

Electrical stimulation has also been suggested for use in the treatment of GERD, wherein the stimulation is supplied to the lower esophageal sphincter (LES). For example, in U.S. Pat. No. 6,901,295, assigned to Endostim, Inc., "A method and apparatus for electrical stimulation of the lower esophageal sphincter (LES) is provided. Electrode sets are placed in the esophagus in an arrangement that induce contractions of the LES by electrical stimulation of the surrounding tissue and nerves. The electrical stimulus is applied by a pulse generator for periods of varying duration and varying frequency so as to produce the desired contractions. The treatment may be short-term or may continue throughout the life of the patient in order to achieve the desired therapeutic effect. The stimulating electrode sets can be used either alone or in conjunction with electrodes that sense esophageal peristalsis. The electrode sets can be placed endoscopically, surgically or radiologically." The referenced invention relies on sensing certain physiological changes in the esophagus, such as changes in esophageal pH, to detect acid reflux. Once a change in esophageal pH is recognized, the system generates an electrical stimulation in an attempt to instantaneously close the LES and abort the episode of acid reflux. U.S. Pat. No. 6,901,295 is hereby incorporated by reference in its entirety.

While current therapy methods and systems utilizing electrical stimulation of body tissues are effective, they are not without their drawbacks. For example, placement of stimulating electrodes is not always ideal. In a system having more than one electrode, a particular electrode might be positioned closer to a target tissue than another electrode, therefore making that particular electrode more effective. In addition, consistent stimulation of target tissues by all electrodes of an electrode set often leads to tissue tolerance and fatigue. Therefore, what is needed is a method and a system that addresses the problems of tissue tolerance and fatigue and electrode placement.

SUMMARY

The present specification discloses a system that enables the switching of electrode polarities such that the better placed electrode or electrodes preferentially stimulate the target tissue while one or more other electrodes become hypopolarizing. Such a system has lower energy requirements and its use results in less tissue tolerance and muscle fatigue.

The present specification also discloses a method of electrically stimulating body tissues comprising the steps of: implanting an electrical stimulation system in a patient, said electrical stimulation system comprising a pulse generator and consisting of a first stimulating electrode operatively connected to said pulse generator and a second stimulating electrode operatively connected to said pulse generator wherein said first stimulating electrode is hyperpolarizing (allowing the tissue to depolarize) and said second stimulating electrode is hypopolarizing (keeping the tissue polarized, acting as a reference); stimulating said body tissues using said first and/or second stimulating electrodes; switching the polarity of said first and/or second electrodes such that said first stimulating electrode becomes hypopolarizing and said second stimulating electrode becomes hyperpolarizing; and, stimulating said body tissues after switching the polarity of said first and/or second electrodes.

The switching of the polarity of said first and second electrodes may be effected manually by a patient or a physician and is programmable. The switching of the polarity of said first and second electrodes may be effected automatically and may be programmable. Optionally, said automatic switching of the polarity of said first and second electrodes occurs at specific times of the day, after certain periods of time, between stimulation sessions, every other pulse, every other nth pulse, every other pulse train, every other nth pulse train, every other day, every other week, or any desired time interval. Optionally, said automatic switching of the polarity of said first and second electrodes occurs when a predetermined measured parameter crosses a predetermined threshold value. The automatic switching of the polarity of said first and second electrodes may occur when a pH level in a lower esophagus of a patient measures above or below a predetermined threshold value.

The present specification also discloses a method of electrically stimulating body tissues comprising the steps of: implanting an electrical stimulation system in a patient, said electrical stimulation system comprising a pulse generator operatively connected to two or more stimulating electrodes wherein a first set of electrodes comprising one or more but not all of said two or more electrodes is hyperpolarizing and a second set of electrodes comprising the electrodes not in said first set is hypopolarizing; measuring the efficacy of electrical stimulation using said first and second sets of electrodes; dissolving said first and second set of electrodes by switching the polarity of at least one electrode of said two or more electrodes to create a third set of electrodes and a fourth set of electrodes wherein said third set, comprising one or more but not all of said two or more electrodes, is hyperpolarizing and said fourth set, comprising the electrodes not in said third set, is hypopolarizing, further wherein said first set is different than said third set and said second set is different than said fourth set; measuring the efficacy of electrical stimulation using said third and fourth sets of electrodes; continuously changing the polarity of one or more electrodes to create a distinct set of hyperpolarizing electrodes different than any previous hyperpolarizing set and a distinct set of hypopolarizing electrodes different than any previous hypopolarizing set until all possible combinations of hyperpolarizing and electrode hypopolarizing sets have been created; and, measuring the efficacy of electrical stimulation using each new pair of sets to determine the electrode polarity configuration exhibiting the best performance.

Optionally, the system used in the method described above comprises three stimulating electrodes. Optionally, the system used in the method described above comprises four stimulating electrodes. Optionally, the system used in the method described above comprises more than four stimulating electrodes.

The present specification also discloses a method of electrically stimulating body tissues comprising the steps of: implanting an electrical stimulation system in a patient, said electrical stimulation system comprising a pulse generator operatively connected to one stimulating electrode, wherein said one stimulating electrode is implanted proximate a target tissue and wherein said implantable pulse generator comprises a metal housing acting as a return electrode, further wherein said implantable pulse generator is implanted away from said target tissue, wherein said one stimulating electrode is hyperpolarizing; measuring the efficacy of electrical stimulation using said one hyperpolarizing stimulating electrode and said housing; switching the polarity of said one stimulating electrode such that it becomes hypopolarizing; and measuring the efficacy of electrical stimulating using said one hypopolarizing stimulating electrode and said housing.

Optionally, the system used in the method described above comprises two or more stimulating electrodes, wherein a first set of electrodes comprising one or more but not all of said two or more electrodes is hyperpolarizing and a second set of electrodes comprising the electrodes not in said first set is hypopolarizing, wherein said method further comprises the steps of: measuring the efficacy of electrical stimulation using said first and second sets of electrodes; dissolving said first and second set of electrodes by switching the polarity of at least one electrode of said two or more electrodes to create a third set of electrodes and a fourth set of electrodes wherein said third set, comprising one or more but not all of said two or more electrodes, is hyperpolarizing and said fourth set, comprising the electrodes not in said third set, is hypopolarizing, further wherein said first set is different than said third set and said second set is different than said fourth set; measuring the efficacy of electrical stimulation using said third and fourth sets of electrodes; continuously changing the polarity of one or more electrodes to create a distinct set of hyperpolarizing electrodes different than any previous hyperpolarizing set and a distinct set of hypopolarizing electrodes different than any previous hypopolarizing set until all possible combinations of hyperpolarizing and electrode hypopolarizing sets have been created; and, measuring the efficacy of electrical stimulation using each new pair of sets to determine the electrode polarity configuration exhibiting the best performance.

Optionally, the system used in the method described above comprises three stimulating electrodes. Optionally, the system used in the method described above comprises four stimulating electrodes. Optionally, the system used in the method described above comprises more than four stimulating electrodes.

The present specification also discloses a method of electrically stimulating body tissues comprising the steps of: implanting an electrical stimulation system in a patient, said electrical stimulation system comprising a pulse generator operatively connected to two or more stimulating electrodes wherein a first set of electrodes comprising one or more but not all of said two or more electrodes is hyperpolarizing and a second set of electrodes comprising the electrodes not in said first set is hypopolarizing; switching the polarity of at least one electrode of said two or more electrodes to dissolve said first and second sets of electrodes and to create a third set of electrodes and a fourth set of electrodes in a response to a worsening of symptoms, wherein said third set, comprising one or more but not all of said two or more electrodes, is hyperpolarizing and said fourth set, comprising the electrodes not in said third set, is hypopolarizing, further wherein said first set is different than said third set and said second set is different than said fourth set; determining if symptoms are improved by electrical stimulation using said third and fourth sets of electrodes; and, continuously changing the polarity of one or more electrodes to create a distinct set of hyperpolarizing electrodes different than any previous hyperpolarizing set and a distinct set of hypopolarizing electrodes different than any previous hypopolarizing set until a pair of sets is created that results in electrical stimulation that improves symptoms.

The present specification also discloses a system for electrically stimulating body tissue comprising a pulse generator and consisting of two stimulating electrodes operatively connected to said pulse generator, wherein a first one of said two stimulating electrodes is hyperpolarizing and a second one of said two stimulating electrodes is hypopolarizing, further wherein the polarity of said two stimulating electrodes is capable of being switched such that said first one of said two stimulating electrodes becomes hypopolarizing and said second one of said two stimulating electrodes becomes hyperpolarizing.

The present specification also discloses a system for electrically stimulating body tissues comprising: a pulse generator operatively connected to two or more stimulating electrodes wherein a first set of electrodes comprising one or more but not all of said two or more electrodes is hyperpolarizing and a second set of electrodes comprising the electrodes not in said first set is hypopolarizing, wherein the polarity of at least one electrode of said two or more electrodes is capable of being switched to dissolve said first and second sets of electrodes and to create a third set of electrodes and a fourth set of electrodes, wherein said third set, comprising one or more but not all of said two or more electrodes, is hyperpolarizing and said fourth set, comprising the electrodes not in said third set, is hypopolarizing, further wherein said first set is different than said third set and said second set is different than said fourth set.

Optionally, said system comprises three stimulating electrodes. Optionally, said system comprises four stimulating electrodes. Optionally, said system comprises more than four stimulating electrodes.

The present specification also discloses a system for electrically stimulating body tissues comprising: a pulse generator operatively connected to one stimulating electrode, wherein said one stimulating electrode is implanted proximate a target tissue and wherein said implantable pulse generator comprises a metal housing acting as a return electrode, further wherein said implantable pulse generator is implanted away from said target tissue, wherein said one stimulating electrode is capable of being switched from a hyperpolarizing state to a hypopolarizing state.

Optionally, the system described above further comprises two or more stimulating electrodes operatively connected to said pulse generator, wherein a first set of electrodes comprising one or more but not all of said two or more electrodes is hyperpolarizing and a second set of electrodes comprising the electrodes not in said first set is hypopolarizing, wherein the polarity of at least one electrode of said two or more electrodes is capable of being switched to dissolve said first and second sets of electrodes and to create a third set of electrodes and a fourth set of electrodes, wherein said third set, comprising one or more but not all of said two or more electrodes, is hyperpolarizing and said fourth set, comprising the electrodes not in said third set, is hypopolarizing, further wherein said first set is different than said third set and said second set is different than said fourth set.

Optionally, said system comprises three stimulating electrodes. Optionally, said system comprises four stimulating electrodes. Optionally, said system comprises more than four stimulating electrodes.

Optionally, the housing of said system comprises hermetic titanium. Optionally, a portion of the housing of said system is coated with an electrically insulating material. Optionally, the housing of said system comprises biocompatible plastic (e.g., epoxy) with an exposed electrode at the surface.

The present specification also discloses a method of electrically stimulating body tissues comprising the steps of: implanting an electrical stimulation system in a patient, said electrical stimulation system comprising a pulse generator and consisting of a first electrode operatively connected to said pulse generator and a second electrode operatively connected to said pulse generator wherein said first electrode is hyperpolarizing and said second electrode is hypopolarizing; applying electrical pulses to said body tissues using said first and second electrodes; switching a polarity of both the first and second electrodes such that said first electrode becomes hypopolarizing and said second electrode becomes hyperpolarizing; and applying electrical pulses to said body tissues after switching the polarity of said first and second electrodes.

Switching of the polarity of said first and second electrodes may be effected manually by a person. Optionally, said switching of the polarity of said first and second electrodes may be effected automatically and may be programmable. The automatic switching of the polarity of said first and second electrodes may occur at a time programmed into a controller of the electrical stimulation system wherein said time may be selected from specific times of the day, after certain periods of time, between stimulation sessions, every other pulse, every other nth pulse, every other pulse train, every other nth pulse train, every other day, every other week, or any desired time interval.

Optionally, said automatic switching of the polarity of said first and second electrodes occurs when a predetermined measured parameter crosses a predetermined threshold value. The automatic switching of the polarity of said first and second electrodes may occur when a pH level in a lower esophagus of the patient measures above or below a predetermined threshold value.

The present specification also discloses a method of electrically stimulating body tissues comprising the steps of: implanting an electrical stimulation system in a patient, said electrical stimulation system comprising a pulse generator operatively connected to two or more electrodes wherein a first set of electrodes comprises one or more but not all of said two or more electrodes and is hyperpolarizing and wherein a second set of electrodes comprises electrodes which are not in said first set and is hypopolarizing; measuring a treatment efficacy of electrical pulses applied by said first and second sets of electrodes; changing a polarity of one or more electrodes and regrouping said electrodes to create a new set of hyperpolarizing electrodes having different electrodes than previous hyperpolarizing sets of electrodes and to create a new set of hypopolarizing electrodes having different electrodes than previous hypopolarizing sets of electrodes; and, measuring a treatment efficacy of electrical pulses applied by each new pair of hyperpolarizing and hypopolarizing sets of electrodes to determine a preferred electrode polarity configuration.

Optionally, the system used in the method described above comprises three stimulating electrodes. Optionally, the system used in the method described above comprises four stimulating electrodes. Optionally, the system used in the method described above comprises more than four stimulating electrodes.

The present specification also discloses a method of electrically stimulating body tissues comprising the steps of: implanting an electrical stimulation system in a patient, said electrical stimulation system comprising a pulse generator operatively connected to one electrode, wherein said one electrode is implanted proximate a target tissue, wherein said implantable pulse generator comprises a metal housing configured as a return electrode, wherein said implantable pulse generator is implanted away from said target tissue, and wherein said one electrode is hyperpolarizing; measuring a treatment efficacy of electrical pulses applied using said one hyperpolarizing stimulating electrode and said housing; switching a polarity of said one electrode such that it becomes hypopolarizing; and measuring a treatment efficacy of electrical pulses applied using said one hypopolarizing electrode and said housing.

The system may comprise two or more electrodes, wherein a first set of electrodes comprising one or more but not all of said two or more electrodes is hyperpolarizing and a second set of electrodes comprising the electrodes not in said first set of electrodes is hypopolarizing, wherein said method further comprises the steps of: measuring a treatment efficacy of electrical pulses applied using said first and second sets of electrodes; switching a polarity of at least one electrode of said two or more electrodes; regrouping said two or more electrodes to create a third set of electrodes and a fourth set of electrodes wherein said third set of electrodes comprises one or more but not all of said two or more electrodes, and is hyperpolarizing, wherein said fourth set of electrodes comprises electrodes not in said third set of electrodes and is hypopolarizing, wherein at least one electrode in said third set of electrodes is different than at least one electrode in said first set of electrodes, and wherein at least one electrode in said fourth set of electrodes is different than at least one electrodes in said second set of electrodes; measuring a treatment efficacy of electrical pulses using said third and fourth sets of electrodes; repeatedly changing a polarity of one or more electrodes to create a new set of hyperpolarizing electrodes different than previous hyperpolarizing sets of electrodes and to create a new set of hypopolarizing electrodes different than previous hypopolarizing sets of electrodes until at least two combinations of hyperpolarizing and hypopolarizing sets of electrodes have been created; and measuring a treatment efficacy of electrical pulses using each set of electrodes to determine an electrode polarity configuration exhibiting an optimum performance.

Optionally, the system used in the method described above comprises three stimulating electrodes. Optionally, the system used in the method described above comprises four stimulating electrodes. Optionally, the system used in the method described above comprises more than four stimulating electrodes.

The present specification also discloses a method of electrically stimulating body tissues, comprising the steps of: implanting an electrical stimulation system in a patient, said electrical stimulation system comprising a pulse generator operatively connected to two or more electrodes wherein a first set of electrodes comprises one or more but not all of said two or more electrodes and is hyperpolarizing and wherein a second set of electrodes comprises the electrodes not in said first set and is hypopolarizing; switching a polarity of at least one electrode of said two or more electrodes to regroup said first and second sets of electrodes into create a third set of electrodes and a fourth set of electrodes, wherein said third set of electrodes comprises one or more but not all of said two or more electrodes and is hyperpolarizing, wherein said fourth set of electrodes comprises electrodes not in said third set of electrodes and is hypopolarizing, and wherein said first set of electrodes is different than said third set of electrodes and said second set of electrodes is different than said fourth set of electrodes; determining if the patient's symptoms are improved by electrical stimulation using said third and fourth sets of electrodes; and repeatedly changing a polarity of one or more electrodes to create a distinct set of hyperpolarizing electrodes different than any previous hyperpolarizing set of electrodes and a distinct set of hypopolarizing electrodes different than any previous hypopolarizing set of electrodes until a pair of electrode sets is created that improves the patient's symptoms.

The present specification also discloses a system for electrically stimulating body tissue, comprising: a pulse generator; a controller; and at least two electrodes operatively connected to said pulse generator and said controller, wherein the controller is programmed to deliver a hyperpolarizing pulse stream through a first one of said two electrodes and is programmed to deliver a hypopolarizing pulse stream through a second one of said two electrodes and wherein the controller is configured to switch polarities of said two electrodes such that said first one of said two electrodes becomes hypopolarizing and said second one of said two electrodes becomes hyperpolarizing.

The present specification also discloses a system for electrically stimulating body tissues, comprising: two or more electrodes; and a pulse generator operatively connected to two or more electrodes and programmed such that a first set of electrodes, which comprises one or more but not all of said two or more electrodes, is hyperpolarizing, and a second set of electrodes, which comprises electrodes not in said first set, is hypopolarizing, wherein the pulse generator is configured to switch a polarity of at least one electrode of said two or more electrodes such that said first and second sets of electrodes are regrouped into a third set of electrodes and a fourth set of electrodes, wherein said third set of electrodes, comprising one or more but not all of said two or more electrodes, is hyperpolarizing and said fourth set of electrodes, comprising the electrodes not in said third set, is hypopolarizing, and wherein said first set of electrodes is different than said third set of electrodes and said second set of electrodes is different than said fourth set of electrodes.

Optionally, said system comprises three stimulating electrodes. Optionally, said system comprises four stimulating electrodes. Optionally, said system comprises more than four stimulating electrodes.

The present specification also discloses a system for electrically stimulating body tissues comprising: an electrode; and a pulse generator, wherein said pulse generator is operatively connected to one electrode, wherein said one electrode is adapted to be implanted proximate a target tissue, wherein said implantable pulse generator comprises a metal housing configured as a return electrode, wherein said implantable pulse generator is adapted to be implanted away a distance further from said target tissue relative to the electrode, and wherein said pulse generator is configured to switch the electrode from a hyperpolarizing state to a hypopolarizing state.

Optionally, said system comprises three stimulating electrodes. Optionally, said system comprises four stimulating electrodes. Optionally, said system comprises more than four stimulating electrodes.

Optionally, the metal housing comprises hermetic titanium. Optionally, a portion of said metal housing is coated with an electrically insulating material. Optionally, the metal housing comprises biocompatible plastic with an exposed electrode at the surface.

The present specification also discloses a method of electrically stimulating body tissues comprising the steps of: implanting an electrical stimulation system in a patient, said electrical stimulation system comprising a pulse generator and a plurality of electrodes operatively connected to said pulse generator where at least one electrode is hyperpolarizing and at least one electrode is hypopolarizing; stimulating said body tissues using said at least one hyperpolarizing electrode and at least one hypopolarizing electrode; switching a polarity of said at least one hypopolarizing electrode and at least one hyperpolarizing electrode such that said hyperpolarizing electrode becomes a hypopolarizing electrode and said hypopolarizing electrode becomes a hyperpolarizing electrode; and stimulating said body tissues after switching the polarity of said hypopolarizing and hyperpolarizing electrodes.

The present specification also discloses a method of electrically stimulating body tissues comprising the steps of: implanting an electrical stimulation system in a patient, said electrical stimulation system comprising a pulse generator and two electrodes operatively connected to said pulse generator where a first electrode is configured as an anode and a second electrode is configured as a cathode; stimulating said body tissues using said anode and cathode; switching a polarity of said cathode and anode such that said cathode becomes an anode and said cathode becomes an anode; and stimulating said body tissues after switching the polarity of said two electrodes.

The aforementioned and other embodiments of the present invention shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings.

DETAILED DESCRIPTION

Figure 1A:
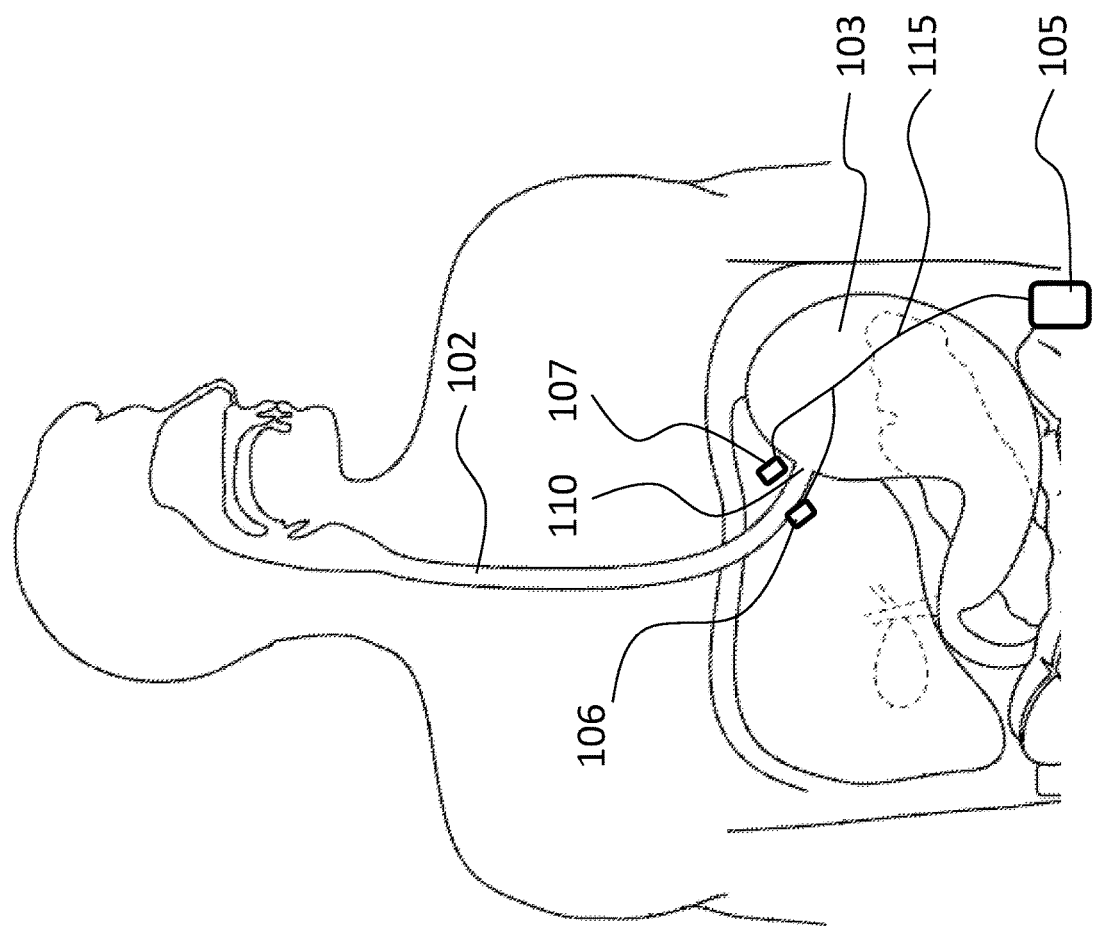
FIG. 1A is an illustration of an upper portion of a gastrointestinal tract of a patient depicting an implantable pulse generator (IPG) with two connected stimulating electrodes positioned proximate the lower esophageal sphincter (LES) and a connected can positioned away from the LES.

The present specification discloses methods and systems of switching the polarity of stimulating electrodes to more effectively treat conditions of biological systems. In one embodiment, a system comprises an implantable pulse generator operatively connected to two or more stimulating electrodes. The stimulating electrodes are positioned proximate a target tissue and electrical pulses are sent from the pulse generator to the electrodes to electrically stimulate said tissue, resulting in an improvement of a specific condition. Improvement can be measured by a decrease in patient reported symptoms, a decrease in patient medication need, and/or diagnostic tests. In various embodiments, the polarity of one or more first electrodes of the system is switched to become hyperpolarizing (depolarizing) while the polarity of one or more second electrodes is switched to become hypopolarizing. The effects of the polarity switch are then observed. If the patient improves, then specific stimulation parameters are developed that focus on the hyperpolarizing electrode(s). If the patient remains the same or worsens, then the electrode polarities are switched again so that the polarity of one or more electrodes different than said one or more first electrodes becomes hyperpolarizing and the polarity of one or more electrodes different than said one or more second electrodes becomes hypopolarizing. Polarity switching continues in this fashion until a hyperpolarizing vs. hypopolarizing electrode combination is found that results in patient improvement.

In another embodiment, a system comprises an implantable pulse generator (IPG) operatively connected to one stimulating electrode and the "can" (the hermetic titanium portion of the IPG housing) that acts as a return electrode. In this embodiment, the stimulating electrode is positioned proximate the target tissue and the can is positioned away from the target tissue, resulting in unipolar stimulation. In one embodiment, the can is implanted in the subcutaneous tissue in the abdomen. In one embodiment, the can has a rectangular cuboid shape with dimensions measuring approximately 40 mm×50 mm×11.5 mm. In another embodiment, wherein the system comprises a microstimulator, the can is implanted in the gastrointestinal (GI) tract, for example, in the stomach or esophagus, or just outside the GI tract within the abdominal cavity. In this embodiment, the can has a rectangular cuboid shape and measures approximately 25 mm×8 mm×5 mm. In one embodiment, the can is composed of titanium. In another embodiment, a portion of the can may be coated with an electrically insulating material to limit the size and/or location of the return electrode. In another embodiment, the can is composed of biocompatible epoxy with an exposed electrode at the surface.

In various embodiments, polarity switching is automatic, triggered manually by the patient and/or physician, based on a preset time or cycle, and/or based on a predetermined threshold requirement.

In various embodiments, the polarity is switched to improve system efficacy, improve system safety, determine system effectiveness, reduce tissue tolerance, reduce muscle fatigue, and/or reduce energy requirements. Occasionally, a stimulating electrode proximate a nerve structure or other body tissue can cause abnormal sensations or discomfort in a patient. In various embodiments, switching the electrodes' polarities avoids discomfort experienced by the patient, thereby improving system safety.

In various embodiments, the condition being treated includes obesity, GERD, urinary incontinence, fecal incontinence, musculoskeletal and/or neurological pain, or any other condition responsive to electrical stimulation therapy.

In the present specification, the term "hyperpolarizing" refers to increasing the polarization of a human body tissue to any level greater than the resting potential of said body tissue and the term "hypopolarizing" refers to decreasing the polarization of a human body tissue to any level less than the resting potential of said body tissue. In one embodiment, an electrode that is hyperpolarizing is configured as a cathode. In one embodiment, an electrode that is hypopolarizing is configured as an anode. In various embodiments of the present specification, one or more stimulating electrodes is hyperpolarizing and acts to hyperpolarize the surrounding tissue while one or more other stimulating electrodes is hypopolarizing and acts to hypopolarize the surrounding tissue. The stimulating electrodes provide signals to the surrounding tissues that are either suprathreshold (excitatory) or subthreshold (nonexcitatory). According to various embodiments of the present specification, the polarizing state of the stimulating electrodes is reversed such that the one or more initially hyperpolarizing electrodes become hypopolarizing while the one or more other initially hypopolarizing electrodes become hyperpolarized.

The present invention is directed toward multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

FIG. 1A is an illustration of an upper portion of a gastrointestinal tract of a patient depicting an implantable pulse generator (IPG) 105 with two connected stimulating electrodes 106, 107 positioned proximate the lower esophageal sphincter (LES) 110. In the pictured embodiment, the IPG 105 is implanted in the subcutaneous tissue of the patient's abdomen and is connected to the stimulating electrodes 106, 107 via an insulated conducting wire 115. The pictured embodiment is used for treating a patient suffering from gastroesophageal reflux disease (GERD). The system comprising the IPG 105 and stimulating electrodes 106, 107 delivers electrical stimulation to the tissues, particularly the muscles and nerves, of and around the lower esophageal sphincter (LES) 110. Electrical stimulation of said tissues results in contraction of the LES muscle, closing the sphincter and preventing the reflux of gastric contents from the stomach 103 into the esophagus 102.

Figure 1B:
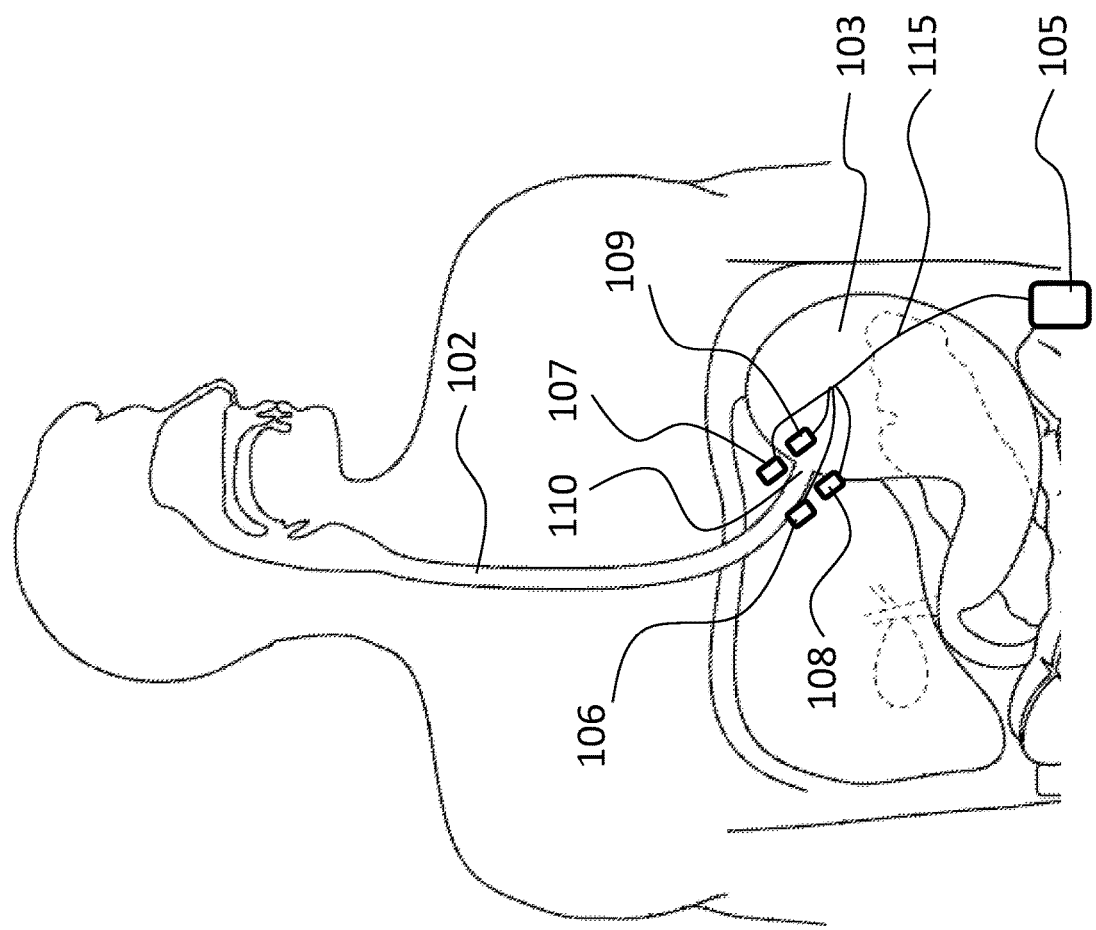
FIG. 1B is an illustration of an upper portion of a gastrointestinal tract of a patient depicting an implantable pulse generator (IPG) with four connected stimulating electrodes positioned proximate the lower esophageal sphincter (LES) and a connected can positioned away from the LES.

FIG. 1B is an illustration of an upper portion of a gastrointestinal tract of a patient depicting an implantable pulse generator (IPG) 105 with four connected stimulating electrodes 106, 107, 108, 109 positioned proximate the lower esophageal sphincter (LES) 110. In the pictured embodiment, the IPG 105 is implanted in the subcutaneous tissue of the patient's abdomen and is connected to the stimulating electrodes 106, 107, 108, 109 via an insulated conducting wire 115. The pictured embodiment is used for treating a patient suffering from gastroesophageal reflux disease (GERD). The system comprising the IPG 105 and stimulating electrodes 106, 107, 108, 109 delivers electrical stimulation to the tissues, particularly the muscles and nerves, of and around the lower esophageal sphincter (LES) 110. Electrical stimulation of said tissues results in contraction of the LES muscle, closing the sphincter and preventing the reflux of gastric contents from the stomach 103 into the esophagus 102.

The IPG comprises a controller, having a memory, and waveform generator that is in electrical and/or data communication with the controller. Alternatively, the IPG may just comprise a pulse generator that combines both the functionality of a controller and waveform generator. The controller may be programmed to generate signals which cause the waveform generator to generate electrical pulse trains having a predefined pulse width, frequency, and/or amplitude. Additionally, the controller may be programmed to cause each electrode, via the waveform generator, to switch from a hyperpolarizing state, or being a cathode, to a hypopolarizing state, or being an anode. The controller may be programmed to switch an individual electrode between generating a hypopolarizing (anode) state and a hyperpolarizing (cathode) state by in a predefined manner, such as having a hypopolarizing and hyperpolarizing state switch in a predefined sequence, having each for a predefined time, or any other sequencing. It should be appreciated that the pulse generator can be programmed in the same manner as the controller.

Figure 2A:
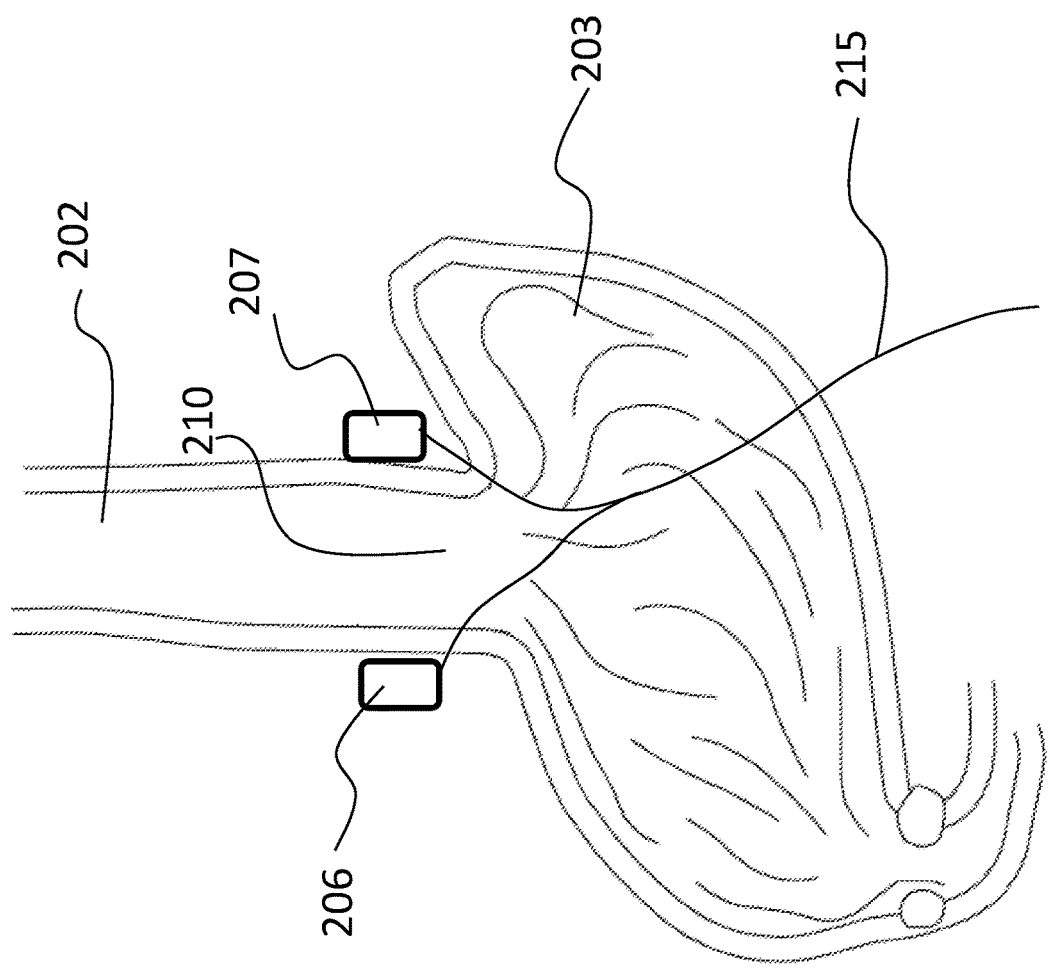
FIG. 2A is an illustration of a stomach and a lower portion of an esophagus of a patient depicting two stimulating electrodes positioned proximate the lower esophageal sphincter (LES)

FIG. 2A is an illustration of a stomach 203 and a lower portion of an esophagus 202 of a patient depicting two stimulating electrodes 206, 207 positioned proximate the lower esophageal sphincter (LES) 210. The electrodes 206, 207 are connected to an IPG (not shown) implanted in the patient's abdomen via an insulated conducting cable 215. Each electrode 206, 207 targets a different portion of tissue surrounding the LES 210. In various embodiments, the electrodes are positioned in a range of 0 mm to 10 mm apart, depending on the application. In one embodiment, the electrodes are positioned at least 2 mm apart to avoid cross-stimulation. The electrodes may be coated with a material such as titanium nitride, conductive polymer, or any other such coating to lower the stimulation threshold, prevent electrolysis, and/or promote tissue ingrowth. The present specification provides preferential stimulation to each of these different tissue portions through polarity switching at each of the electrodes 206, 207.

In one embodiment, after implantation, all electrodes begin as non-polarized. In various embodiments, when stimulation starts, one or more electrodes become hyperpolarizing (depolarizing) while one or more other electrodes become hypopolarizing. In one embodiment involving bipolar stimulation, a first target electrode is hyperpolarizing (depolarizing) while a second electrode is hypopolarizing. For example, in an embodiment involving stimulation of the lower esophageal sphincter (LES), a first electrode in a high pressure zone in the LES becomes hyperpolarizing (depolarizing) while a second electrode that is partially at the LES and partially outside the LES is hypopolarizing.

In one embodiment, the polarity of electrode 206 is hyperpolarizing while the polarity of electrode 207 is switched to become hypopolarizing. If the patient improves, then the physician knows electrode 206 is positioned close to target neural fibers or tissue. In one embodiment, the polarity of each electrode 206, 207 can be switched independently from the polarity of any of the other electrodes 206, 207. Therefore, the physician and/or patient can try both possible electrode polarity combinations to discover the more effective configuration. Having less than all of the electrodes hyperpolarizing reduces energy consumption of the system. Additionally, tissue tolerance and fatigue is reduced proximate the at least one hypopolarizing electrode.

Safety of the system is also enhanced as fewer body tissues are subjected to electrical energy. Though a system comprising two stimulating electrodes is discussed with reference to FIG. 2A, other embodiments including more than two electrodes, such as three or four electrodes as described below, are also possible.

Figure 2B:
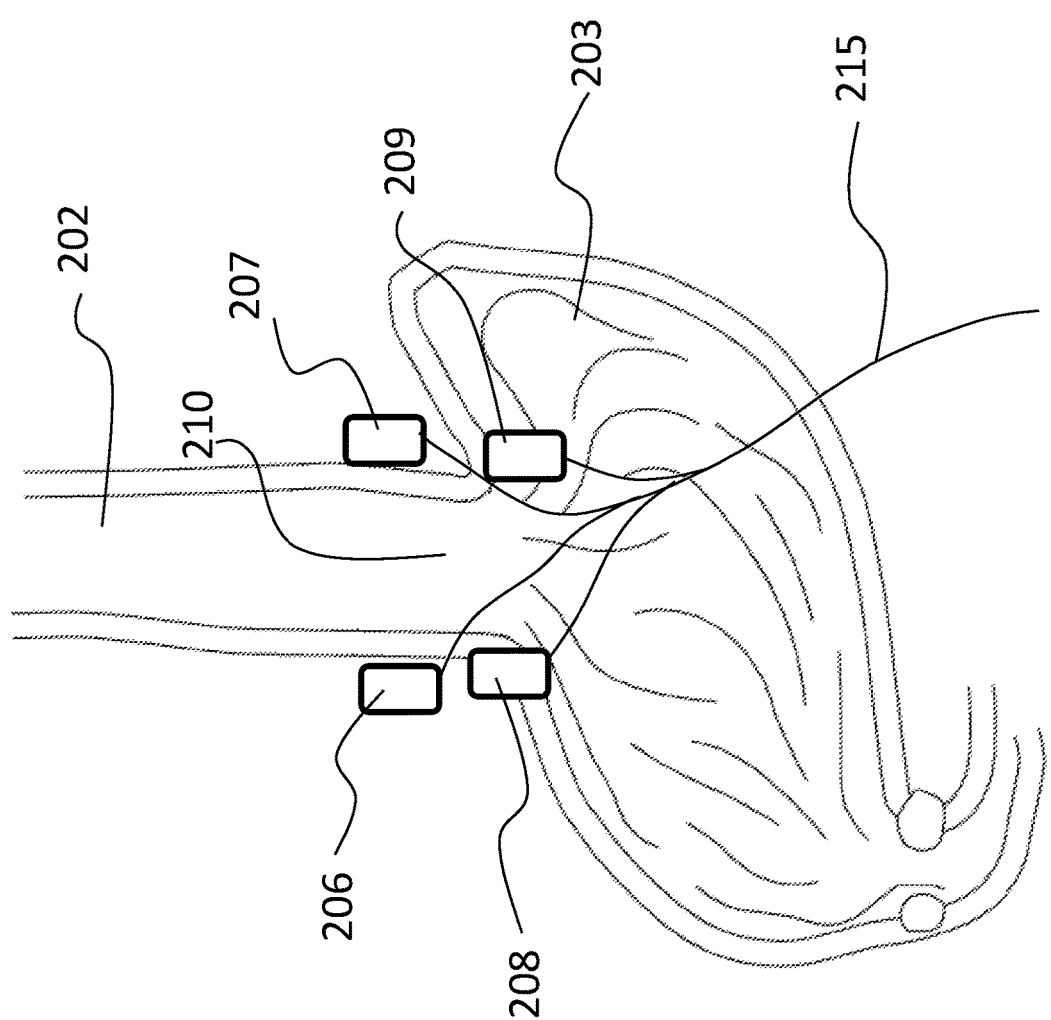
FIG. 2B is an illustration of a stomach and a lower portion of an esophagus of a patient depicting four stimulating electrodes positioned proximate the lower esophageal sphincter (LES)

FIG. 2B is an illustration of a stomach 203 and a lower portion of an esophagus 202 of a patient depicting four stimulating electrodes 206, 207, 208, 209 positioned proximate the lower esophageal sphincter (LES) 210. The electrodes 206, 207, 208, 209 are connected to an IPG (not shown) implanted in the patient's abdomen via an insulated conducting cable 215. Each electrode 206, 207, 208, 209 targets a different portion of tissue surrounding the LES 210. In various embodiments, the electrodes are positioned in a range of 0 mm to 10 mm apart, depending on the application. In one embodiment, the electrodes are positioned at least 2 mm apart to avoid cross-stimulation. The present specification provides preferential stimulation to each of these different tissue portions through various combinations of polarity switching at each of the electrodes 206, 207, 208, 209.

In one embodiment, the polarity of electrode 206 is switched to become hyperpolarizing while the polarity of electrodes 207, 208, 209 is switched to become hypopolarizing. If the patient improves, then the physician knows electrode 206 is positioned close to target neural fibers or tissue. In one embodiment, the polarity of each electrode 206, 207, 208, 209 can be switched independently from the polarity of any of the other electrodes 206, 207, 208, 209. Therefore, the physician and/or patient can try any possible electrode polarity combination (for example, electrodes 207 and 209 hyperpolarizing and electrodes 206 and 208 hypopolarizing) to discover the most effective configuration. Again, having less than all of the electrodes hyperpolarizing reduces energy consumption of the system. Tissue tolerance and fatigue is reduced proximate the at least one hypopolarizing electrode. Safety of the system is also enhanced as fewer body tissues are subjected to electrical energy.

In other embodiments, the system comprises an implantable pulse generator (IPG) connected to one or more electrodes wherein only one electrode receives stimulating energy and the can acts as the return electrode. In this embodiment, the stimulating electrode is positioned proximate the target tissue and the can is positioned away from the target tissue, resulting in unipolar stimulation. In one embodiment, the can is implanted in the subcutaneous tissue in the abdomen. In another embodiment, wherein the system comprises a microstimulator, the can is implanted in the gastrointestinal (GI) tract, for example, in the stomach or esophagus, or just outside the GI tract within the abdominal cavity. For example, referring simultaneously to FIGS. 2A and 2B, in various embodiments, only one of the electrodes 206, 207, 208, 209 receives stimulating energy while the can or IPG (not shown) functions as the return electrode.

In one embodiment, the polarization switch discussed in the above embodiments is triggered manually. The patient or physician switches the polarity of one or more electrodes using a wired or wireless external programming device. The patient can switch polarity whenever he experiences pain or other symptoms. The physician can switch polarity after implantation or at follow up office visits to test effectiveness and determine the best electrode polarity combination for therapy.

In another embodiment, the polarization switch is triggered automatically. In this embodiment, the patient does not have the ability to control the polarity switch, thereby eliminating the possibility of system ineffectiveness resulting from excessive polarity switching. In various embodiments, automatic polarity switching is programmed to occur at specific times of the day, after certain periods of time, or between stimulation sessions. Additionally, in various embodiments, automatic polarity switching is programmed to occur every other pulse, every other nth pulse, every other pulse train, every other nth pulse train, every other day, every other week, or any other desired time interval. In one embodiment, the automatic polarity switching is programmable. In various embodiments, automatic polarity switching is triggered when a measured parameter crosses a predetermined threshold value. For example, in an embodiment wherein a patient suffers from GERD, the polarity of selected electrodes switch when the measured pH of the lower esophagus drops below a predetermined threshold value. This automatic polarity switching allows for improved efficacy and safety of stimulation plus decreased tolerance of fatigue in the stimulated tissue. Additionally, such therapy allows for reduced requirement of total energy by stimulating distinct areas of the targeted tissue, thereby providing an additive or synergistic effect on the efficacy.

Figure 3:
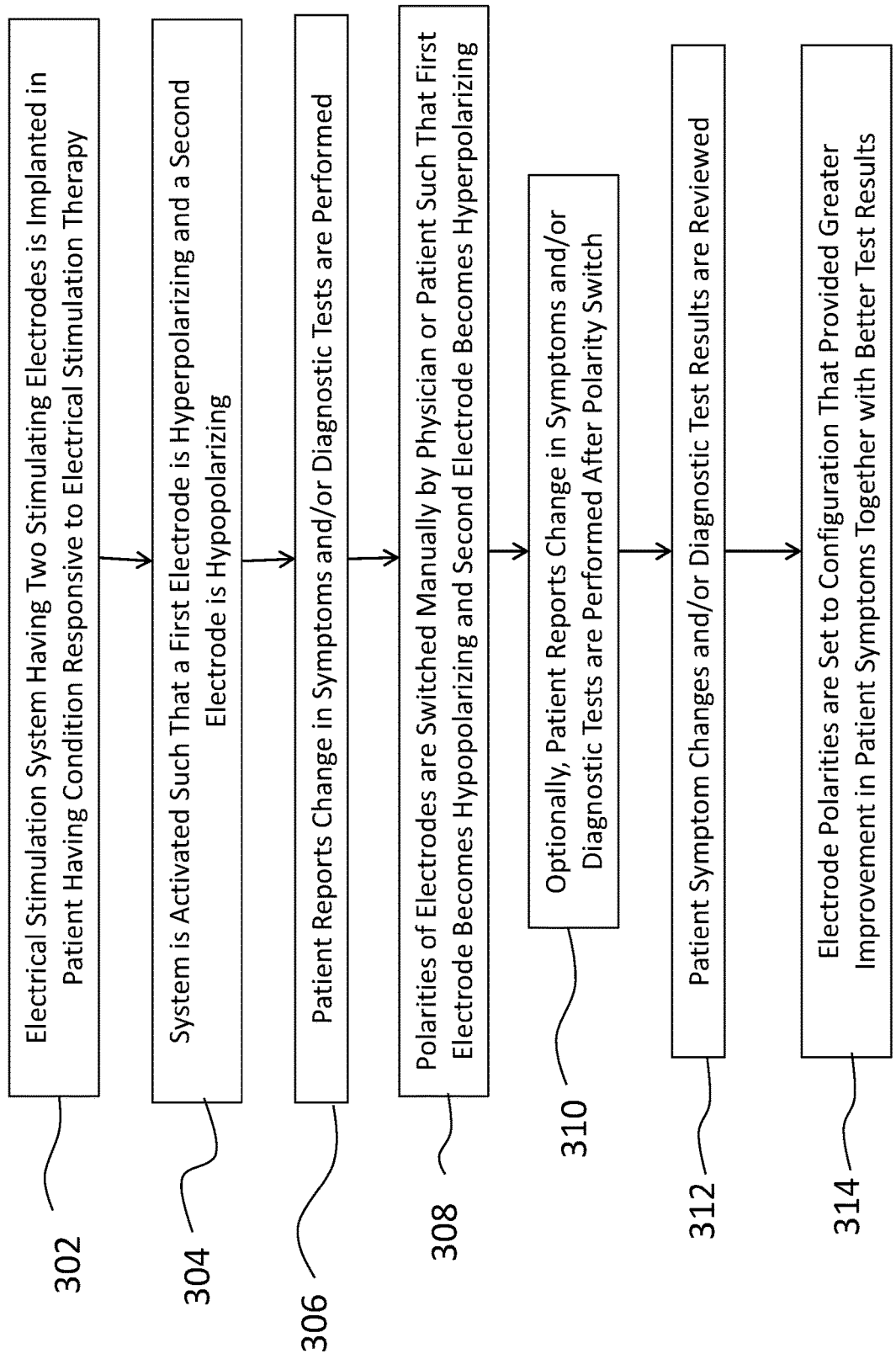
FIG. 3 is a flowchart listing the steps involved in one embodiment of a method of determining maximum efficacy of electrical stimulation of a target tissue by manually switching polarity of electrodes of a newly implanted stimulation system.

FIG. 3 is a flowchart listing the steps involved in one embodiment of a method of determining maximum efficacy of electrical stimulation of a target tissue by manually switching polarity of electrodes of a newly implanted stimulation system. At step 302, an electrical stimulation system having two stimulating electrodes is implanted in a patient having a condition responsive to electrical stimulation therapy. The system is activated at step 304 such that a first electrode is hyperpolarizing and a second electrode, or the can, is hypopolarizing. The patient reports any change in symptoms and/or diagnostic tests are performed at step 306. The diagnostic tests are designed to inform the physician if stimulation with the current electrode polarity configuration is having a beneficial effect and to what degree. For example, in one embodiment of a patient suffering from GERD, manometry of the lower esophagus is performed to determine if esophageal pressure is improving. At step 308, the polarities of the electrodes are switched manually by the physician or the patient such that the first electrode, or the can, becomes hypopolarizing and the second electrode becomes hyperpolarizing. After the polarity switch, in some embodiments at step 310, the patient reports any change in symptoms and/or diagnostic tests are again performed. The patient symptom changes and/or diagnostic test results are reviewed at step 312. At step 314, the electrode polarities are set to the configuration that provided the greater improvement in patient symptoms together with the better test results.

Figure 4:
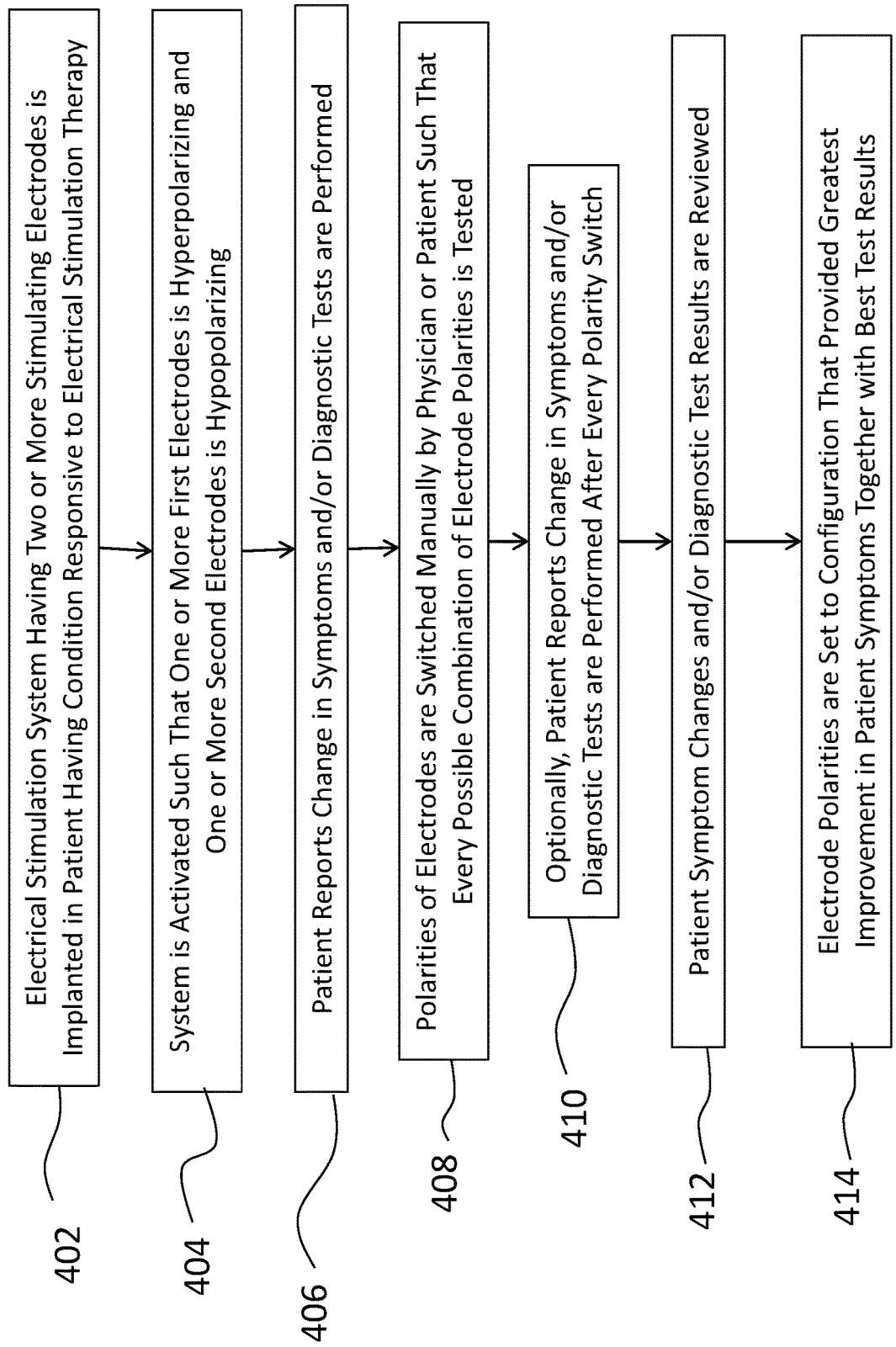
FIG. 4 is a flowchart listing the steps involved in another embodiment of a method of determining maximum efficacy of electrical stimulation of a target tissue by manually switching polarity of electrodes of a newly implanted stimulation system; and, FIG. 5 is a flowchart listing the steps involved in one embodiment of a method of manually switching polarity of electrodes of an implanted stimulation system in an effort to improve patient symptoms.

FIG. 4 is a flowchart listing the steps involved in another embodiment of a method of determining maximum efficacy of electrical stimulation of a target tissue by manually switching polarity of electrodes of a newly implanted stimulation system. At step 402, an electrical stimulation system having two or more stimulating electrodes is implanted in a patient having a condition responsive to electrical stimulation therapy. The system is activated at step 404 such that one or more first electrodes is hyperpolarizing and one or more second electrodes, or the can, is hypopolarizing. The patient reports any change in symptoms and/or diagnostic tests are performed at step 406. The diagnostic tests are designed to inform the physician if stimulation with the current electrode polarity configuration is having a beneficial effect and to what degree. For example, in one embodiment of a patient suffering from GERD, manometry of the lower esophagus is performed to determine if esophageal pressure is improving. At step 408, the polarities of the electrodes are switched manually by the physician or the patient such that every possible combination of electrode polarities is tested. After each polarity switch, in some embodiments at step 410, the patient reports any change in symptoms and/or diagnostic tests are again performed. Once all combinations have been tested, the patient symptom changes and/or diagnostic test results are reviewed at step 412. At step 414, the electrode polarities are set to the configuration that provided the greatest improvement in patient symptoms together with the best test results.

Figure 5:
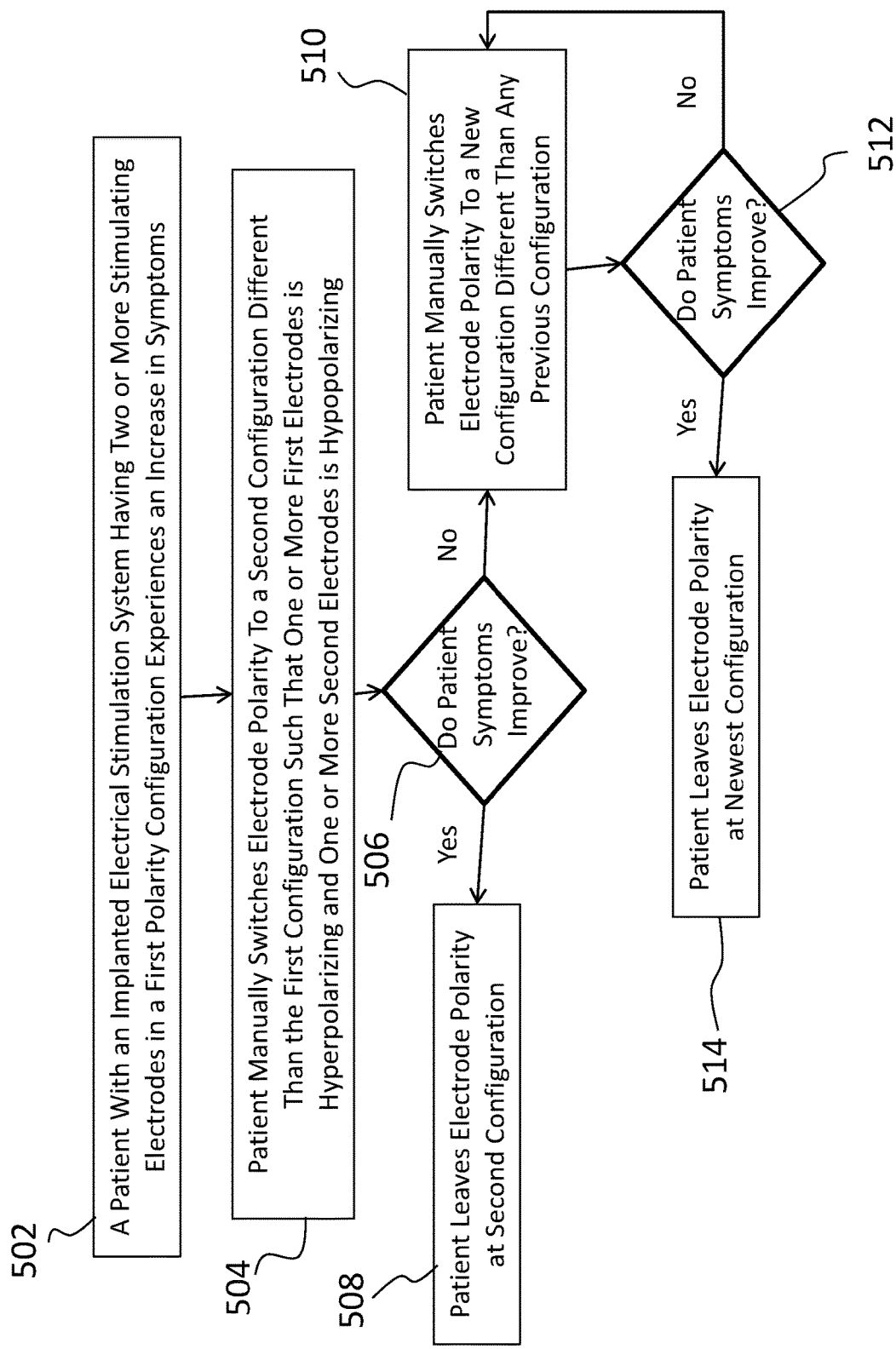

FIG. 5 is a flowchart listing the steps involved in another embodiment of a method of manually switching polarity of electrodes of an implanted stimulation system in an effort to improve patient symptoms or reduce side effects. At step 502, a patient with an implanted electrical stimulation system having two or more stimulating electrodes in a first polarity configuration experiences an increase in symptoms or side effects. The patient manually switches electrode polarity to a second configuration different than the first configuration such that one or more first electrodes is hyperpolarizing and one or more second electrodes, or the can, is hypopolarizing at step 504. At step 506, the patient determines if his symptoms have improved or side effects have reduced after the polarity switch. If the symptoms have improved or the side effects have reduced, then the patient leaves the electrode polarity at the second configuration at step 508. If the symptoms have not improved or the side effects have not reduced, then, at step 510, the patient manually switches the electrode polarity to a new configuration different than any previous configuration. The patient then determines again if his symptoms have improved or the side effects have reduced at step 512. If the symptoms have improved or the side effects have reduced, the patient leaves the electrode polarity at the newest configuration at step 514. If the symptoms have not improved or the side effects have not reduced, the patient tries a different polarity configuration at step 510 and continues trying new configurations until one provides better relief from his symptoms or side-effects.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method of electrically stimulating body tissues comprising the steps of:
   implanting an electrical stimulation system in a patient, said electrical stimulation system comprising a pulse generator and consisting of a first electrode operatively connected to said pulse generator and a second electrode operatively connected to said pulse generator wherein said first electrode is hyperpolarizing and said second electrode is hypopolarizing;
   applying electrical pulses to said body tissues using said first and second electrodes;
   measuring a treatment efficacy of electrical pulses applied using the hyperpolarizing first electrode and the hypopolarizing second electrode by determining if the patient's symptoms related to gastroesophageal reflux disease improve or worsen;
   based upon the measuring of treatment efficacy, switching a polarity of both the first and second electrodes such that said first electrode becomes hypopolarizing and said second electrode becomes hyperpolarizing; and
   applying electrical pulses to said body tissues after switching the polarity of said first and second electrodes.

2. The method of electrically stimulating body tissues of claim 1, wherein said switching of the polarity of said first and second electrodes is achieved manually by a person.

3. The method of electrically stimulating body tissues of claim 1, wherein said switching of the polarity of said first and second electrodes is achieved automatically and is programmable.

4. The method of electrically stimulating body tissues of claim 3, wherein said automatic switching of the polarity of said first and second electrodes occurs at a time programmed into a controller of the electrical stimulation system and wherein said time is selected from specific times of the day, after certain periods of time, between stimulation sessions, every other pulse, every other nth pulse, every other pulse train, every other nth pulse train, every other day, every other week, or any desired time interval.

5. The method of electrically stimulating body tissues of claim 3, wherein said automatic switching of the polarity of said first and second electrodes occurs when a predetermined measured parameter crosses a predetermined threshold value.

6. The method of electrically stimulating body tissues of claim 5, wherein said automatic switching of the polarity of said first and second electrodes occurs when a pH level in a lower esophagus of the patient measures above or below a predetermined threshold value.

7. A method of electrically stimulating body tissues comprising the steps of:
   implanting an electrical stimulation system in a patient, said electrical stimulation system comprising a pulse generator operatively connected to one electrode, wherein said one electrode is implanted proximate a target tissue, wherein said implantable pulse generator comprises a metal housing configured as a return electrode, wherein said implantable pulse generator is implanted away from said target tissue, and wherein said one electrode is hyperpolarizing;
   measuring a first treatment efficacy of electrical pulses applied using said one hyperpolarizing stimulating electrode and said housing by determining if the patient's symptoms related to gastroesophageal reflux disease improve or worsen;
   based upon the measuring of the first treatment efficacy, switching a polarity of said one electrode such that it becomes hypopolarizing; and
   measuring a second treatment efficacy of electrical pulses applied using said one hypopolarizing electrode and said housing by determining if the patient's symptoms related to gastroesophageal reflux disease improve or worsen.

8. The method of electrically stimulating body tissues of claim 7, wherein said system comprises two or more electrodes, wherein a first set of electrodes comprising one or more but not all of said two or more electrodes is hyperpolarizing and a second set of electrodes comprising the electrodes not in said first set of electrodes is hypopolarizing, said method further comprising the steps of:
   measuring a third treatment efficacy of electrical pulses applied using said first and second sets of electrodes by determining if the patient's symptoms related to gastroesophageal reflux disease improve or worsen;

based upon the measuring of the third treatment efficacy, switching a polarity of at least one electrode of said two or more electrodes;

regrouping said two or more electrodes to create a third set of electrodes and a fourth set of electrodes wherein said third set of electrodes comprises one or more but not all of said two or more electrodes, and is hyperpolarizing, wherein said fourth set of electrodes comprises electrodes not in said third set of electrodes and is hypopolarizing, wherein at least one electrode in said third set of electrodes is different than at least one electrode in said first set of electrodes, and wherein at least one electrode in said fourth set of electrodes is different than at least one electrodes in said second set of electrodes;

measuring a fourth treatment efficacy of electrical pulses using said third and fourth sets of electrodes by determining if the patient's symptoms related to gastroesophageal reflux disease improve or worsen;

based upon the measuring of the fourth treatment efficacy, repeatedly changing a polarity of one or more electrodes to create a new set of hyperpolarizing electrodes different than previous hyperpolarizing sets of electrodes and to create a new set of hypopolarizing electrodes different than previous hypopolarizing sets of electrodes until at least two combinations of hyperpolarizing and hypopolarizing sets of electrodes have been created; and measuring a fifth treatment efficacy of electrical pulses using each set of electrodes to determine an electrode polarity configuration exhibiting an optimum performance.

9. The method of electrically stimulating body tissues of claim 8, wherein said system comprises three electrodes.

10. The method of electrically stimulating body tissues of claim 8, wherein said system comprises four electrodes.

11. The method of electrically stimulating body tissues of claim 8, wherein said system comprises more than four electrodes.

12. A method for electrically stimulating body tissues using a first electrode, a second electrode and a pulse generator, wherein said pulse generator is operatively connected to the first electrode and the second electrode, wherein the first electrode is adapted to be implanted proximate a target tissue, wherein said pulse generator is adapted to be implanted away a distance further from said target tissue relative to the electrode, and wherein said pulse generator is configured to switch the first electrode from a hyperpolarizing state to a hypopolarizing state and switch the second electrode from a hypopolarizing state to a hyperpolarizing state, the method comprising:

measuring a first treatment efficacy of electrical pulses applied using the hyperpolarizing first electrode and the hypopolarizing second electrode by determining if the patient's symptoms related to gastroesophageal reflux disease improve or worsen;

based upon the measuring of the first treatment efficacy, switching a polarity of the first electrode such that it becomes hypopolarizing and the second electrode such that it becomes hyperpolarizing; and measuring a second treatment efficacy of electrical pulses applied using the hypopolarizing first electrode and the hyperpolarizing second electrode by determining if the patient's symptoms related to gastroesophageal reflux disease improve or worsen.

13. The method for electrically stimulating body tissues of claim 12, further comprising using a third electrode.

14. The method for electrically stimulating body tissues of claim 12, further comprising using a fourth electrode.

15. The method for electrically stimulating body tissues of claim 12, further comprising using more than four electrodes.

16. The method for electrically stimulating body tissues of claim 12, wherein said implantable pulse generator comprises a metal housing configured as a return electrode and wherein said metal housing is made from hermetic titanium.

17. The method for electrically stimulating body tissues of claim 16, wherein a portion of said metal housing is coated with an electrically insulating material.

18. The method for electrically stimulating body tissues of claim 16, wherein said metal housing comprises biocompatible plastic with an exposed electrode at the surface.

* * * * *